(12) United States Patent
Dasgupta et al.

(10) Patent No.: US 10,416,137 B2
(45) Date of Patent: Sep. 17, 2019

(54) ELECTRODIALYTIC CAPILLARY SUPPRESSOR FOR SUPPRESSED CONDUCTOMETRIC ION CHROMATOGRAPHY

(71) Applicants: Purnendu K. Dasgupta, Arlington, TX (US); Weixiong Huang, Arlington, TX (US)

(72) Inventors: Purnendu K. Dasgupta, Arlington, TX (US); Weixiong Huang, Arlington, TX (US)

(73) Assignee: BOARD OF REGENTS, UNIVERSITY OF TEXAS SYSTEM, Austin, TX (US)

( * ) Notice: Subject to any disclaimer, the term of this patent is extended or adjusted under 35 U.S.C. 154(b) by 320 days.

(21) Appl. No.: 15/258,493

(22) Filed: Sep. 7, 2016

(65) Prior Publication Data
US 2018/0065089 A1    Mar. 8, 2018

(51) Int. Cl.
*G01N 30/96* (2006.01)
*B01D 15/24* (2006.01)
(Continued)

(52) U.S. Cl.
CPC .............. *G01N 30/96* (2013.01); *B01D 15/24* (2013.01); *B01D 15/361* (2013.01);
(Continued)

(58) Field of Classification Search
CPC ...... B01D 61/42; B01D 61/422; B01D 61/44; B01D 61/46; C02F 1/4693
See application file for complete search history.

(56) References Cited

U.S. PATENT DOCUMENTS 5,352,360 A    10/1994  Stillian et al.
7,582,482 B2    9/2009  Dasgupta et al.
(Continued)

FOREIGN PATENT DOCUMENTS

EP    1 685 886    8/2006

OTHER PUBLICATIONS

WO, International Search Report and Written Opinion issued in corresponding International Patent Application No. PCT/US2017/049827, 10 pages (dated Nov. 7, 2017).
(Continued)

*Primary Examiner* — Salil Jain
(74) *Attorney, Agent, or Firm* — Thompson Hine LLP

(57) ABSTRACT

An electrodialytic device for ion chromatography, including aspects functioning as an eluent suppressor device and aspects functioning as an eluent generator device. In general, the device includes a monolithic block of ionomeric polymer material having (1) a first channel with an inlet port, an outlet port, and an active length of exposed polymer material disposed therebetween, (2) a second channel having an inlet port, an outlet port, and an active length of exposed polymer material disposed therebetween, (3) a first and second at-least-partially exposed electrodes positioned in electrical communication with the second channel, with the second electrode disposed, at least in part, across the second channel from the first electrode. A current flowing between the electrodes will drive an electrodialytic migration of ions between the active lengths, from an eluent stream in the case of a suppression device or into an eluent stream in the case of a generator device.

20 Claims, 19 Drawing Sheets

(51) Int. Cl.
*B01D 15/36* (2006.01)
*B01D 61/48* (2006.01)
B01D 61/42 (2006.01)
B01D 63/06 (2006.01)

(52) U.S. Cl.
CPC .......... *B01D 61/422* (2013.01); *B01D 63/066* (2013.01); *G01N 2030/965* (2013.01)

(56) References Cited

U.S. PATENT DOCUMENTS

| | | | | |
|---|---|---|---|---|
| 2009/0127200 | A1* | 5/2009 | Dasgupta | B01D 15/166 210/659 |
| 2012/0264920 | A1* | 10/2012 | Wang | B01D 15/125 530/388.1 |
| 2013/0048498 | A1 | 2/2013 | Dasgupta et al. | |

OTHER PUBLICATIONS

Dasgupta. Automated Measurement of Atmospheric Trace Gases Diffusion-Based Collection and Analysis. Measurement Challenges in Atmospheric Chemistry Advances in Chemistry; American Chemical Society, 232 (1993) 41-90.
Dasgupta. Annular Helical Suppressor for Ion Chromatography. Analytical Chemistry American Chemical Society 56 (1984) 103-105. 232 (1993) 41-90.
Dasgupta and Bao. Suppressed Conductometric Capillary Electrophoresis Separation Systems. Anal. Chem. 65 (1993) 1003-1011.
Rabin et al. New membrane-based electrolytic suppressor device for suppressed conductivity detection in ion chromatography, Journal of Chromatography, 640 (1993) 97-109.
Stillian. An Improved Suppressor for Ion Chromatography. LC 3 (1985) 802, 806, 808, 812.
Christian, Dasgupta, and Schug. Equipment for HPLC. Analytical Chemistry, 7th Ed. Wiley, New York, 2014 pp. 665-691.
Castellan, G.W. Atomic Spectroscopy. Physical Chemistry. Addison-Wesley, London, 1964. Table of Contents and p. 588.

Huang et al. Five-electrode direct current suppressor-detector combiner for ion chromatography: an integration of eluent suppression and resistance detection. Analyst, 2011, 136, 901-903 1901.
Kuban et al. Capillary ion chromatography. J. Sep. Sci. 2004, 27, 1441-1457.
Rokushika et al. Micro Column Ion Chromatography With a Hollow Fibre Suppressor. Journal of Chromatoqruphy, 260 (1983) 81-87.
Stevens et al. Packed Hollow Fiber Suppressors for Ion Chromatography. Analytical Chemistry, vol. 54, No. 7, Jun. 1982.
Dasgupta. Automated Measurement of Atmospheric Trace Gases Diffusion-Based Collection and Analysis. American Chemical Society 1993.
Dasgupta et al. Black Box Linearization for Greater Linear Dynamic Range: the Effect of Power Transforms on the Representation of Data. Anal. Chem. 2010, 82, 10143-10150.
Zhang et al. Capillary Scale Admittance Detection. Anal. Chem. 2014, 86, 11538-11546.
Yang et al. An Open Tubular Ion Chromatograph. Anal. Chem. 2014, 86, 11554-11561.
Wouters et al. Design and performance evaluation of a microfluidic ion-suppression module for anion-exchange chromatography. Journal of Chromatography A, 1355 (2014) 253-260.
Small et al. Electrically Polarized Ion-Exchange Beds in Ion Chromatography: Ion Reflux. Anal. Chem. 1998, 70, 2205-2212.
Gjerde et al. Suspension Postcolumn Reaction Detection Method for Liquid Chromatography. Anal. Chem. 1990, 62, 612-615.
Kuban et al. Vertically Stratified Flows in Microchannels. Computational Simulations and Applications to Solvent Extraction and Ion Exchange. Anal. Chem. 2003, 75, 3549-3556.
Small et al. Novel Ion Exchange Chromatographic Method Using Conductimetric Detection. Analytical Chemistry, vol. 47, No. 11, Sep. 1975.
Stevens et al. Hollow Fiber Ion-Exchange Suppressor for Ion Chromatography. Anal. Chem. 1981, 53, 1488-1492.
Dasgupta. Annular Helical Suppressor for Ion Chromatography. 1983 American Chemical Society.
Tian et al. Effect of Suppression Efficiency on Sensitivity in Ion Chromatography. Journal of Chromatography, 439 (1988) 151-157.
Haddad et al. Developments in suppressor technology for inorganic ion analysis by ion chromatography using conductivity detection. Journal of Chromatography A, 1000 (2003) 725-742.

* cited by examiner

ELECTRODIALYTIC CAPILLARY SUPPRESSOR FOR SUPPRESSED CONDUCTOMETRIC ION CHROMATOGRAPHY

GOVERNMENT SUPPORT

This invention was made with government support under (Grant No. NNX15AM76G) awarded by NASA. The government has certain rights in the invention.

BACKGROUND

Suppressor devices have become a cornerstone of Suppressed Conductometric Ion Chromatography (SCIC) [1] systems, which are used for the separation and determination of inorganic and many small organic ions [2]. Since electrical conductivity is a universal property of ions, conductance measurement is the most commonly used detection technique in ion chromatography (IC) systems, where an ionic eluent at millimolar concentrations is used to elute analyte ions, typically present at micromolar ($\mu$M) concentrations (~3 orders of magnitude less than the eluent concentration), from a separation column. Because the equivalent conductance of the eluent ($\lambda_{E-}$) and the analyte ions ($\lambda_{A-}$) differ, it is possible to conductometrically detect eluting ions directly after the separation column (Non-Suppressed Ion Chromatography (NSIC)), but the sensitivity is poor as the difference in conductivity $|(\lambda_A - \lambda_{E-})|$ is small and the background conductivity is high. A suppressor serves to convert the eluent to a very weak electrolyte (weak acid/base or water), greatly reducing (suppressing) the background conductivity caused by the eluent. Analyte signals are also enhanced because their counterions are substituted by more conductive hydronium or hydroxide ions. By reducing the background conductivity (and hence noise level) by ~2 orders of magnitude and improving the analyte sensitivity by nearly an order of magnitude, the limits of detection (LODs) of SCIC systems can be improved by 2 to 3 orders of magnitude relative to NSIC.

A variety of suppressors have been developed for such systems, from early packed-column [1], hollow-fiber [3,4], and micromembrane suppressors [5], to modern electrodialytic membrane-based [6,7] and continuously regenerated packed-column suppressors [8], as well as colloidal ion exchangers [9]. Microfluidic suppressors have also been described [10-12]. By exploiting the electrolytic decomposition of water to generate the hydronium or hydroxide ions necessary for suppression reactions, an electrodialytic membrane-based suppressor can be operated in self-regenerating mode without the addition of any regenerant, and permits high dynamic suppression capacity with a low dead volume.

Capillary ion chromatography (CIC) is gaining attention because of its low sample and eluent consumption and high efficiency. Suppressed Conductometric Capillary Ion Chromatography (SCCIC) was first demonstrated by Rokushika et al. [13], who coupled a resin-packed fused-silica capillary column (0.19 mm i.d.) to a sulfonated hollow fiber tube (0.2 mm i.d.×10 mm) functioning as a suppressor. CIC technology was last reviewed by Kuban and Dasgupta [14]. Strategies used in larger-scale systems, such as integration of the suppressor and detector [15], can reduce post-suppressor broadening but do little for broadening in the suppressor and do not address the issue of dispersion in any connection between the separation column and the suppressor. Strategies previously used to reduce broadening in macroscale suppressors, such as packing perfluorosulfonate cation exchanger (Nafion®) tubing with inert beads [16], filling with nylon monofilament [4], etc., are simply inapplicable in CIC-scale systems.

SUMMARY

An electrodialytic capillary suppressor for Suppressed Conductometric Open Tubular Ion Chromatography (SC-OTIC) is disclosed. In a preferred embodiment, the suppressor comprises a monolithic block of an ionomeric polymer, i.e., a solid polymer ion exchange material or solid mixture of polymers substantially including a polymer ion exchange material. The block includes at least two channels: a first, regenerant channel, which for CIC purposes may be a sub-millimeter diameter channel, for passage of regenerant water; and a second, suppression channel, which for CIC purposes may be made with a needle of a diameter slightly smaller than the outer diameter of separation/detection capillaries to be inserted into the block, for passage of an eluent/analyte stream prior to conductometric detection. An electrode, which is preferably partially insulated so as to direct an applied electrical current through an active zone within the block, i.e., a zone in which ions migrate between lengths of exposed polymer material within the channels in response to the applied electrical current, is positioned in electrical communication with the second channel. For example, the electrode may be positioned (1) within the active length of the first channel (the length of exposed polymer material within the first channel) or (2) or in contact with the block at least on a side, relative to the first channel, opposite to the second channel. A counter electrode, which is preferably partially insulated so as to direct the applied electrical current through the active zone, is also positioned in electrical communication with the second channel. For example, the counter electrode may be positioned (1) in contact with the block at least on a side, relative to the second channel, opposite to the first channel or (2) within an active length of an optional third channel positioned on a side, relative to the second channel, opposite to the first channel. To suppress practical eluent concentrations, the channels should have active lengths, i.e., lengths of exposed polymer material not shielded by inlet or outlet structures such as inserted tubing, of at least 0.4 mm. To provide adequate suppression while curtailing dispersion within the device, the ends of separation and detection capillary tubes may be inserted directly into the suppression channel with their respective tips spaced from 0.4 mm to 1.5 mm apart. With a sufficiently long active suppression length, the device is capable of suppressing a 100 mM alkali hydroxide eluent flowing at 100 nL/min (10 neq/min). With such a suppressor coupled to an AS18 latex coated surface-sulfonated cyclo-olefin Polymer (COP) capillary column of 28 μm i.d. and using an on-capillary admittance detector (AD), the feasibility of both isocratic and gradient SC-OTIC is shown. At an eluent flow rate of 170 nL/min (substantially above the Van Deemter optimum), the plate count for fluoride can exceed 70,000 plates/m under isocratic conditions. The peak dispersion observed with the suppressor described herein is demonstrably superior to that produced by prior devices known to the applicants.

An electrodialytic eluent generator device for Suppressed Conductometric Open Tubular Ion Chromatography (SC-OTIC) is also disclosed. In a preferred embodiment, the block includes at least two channels: a first, regenerant channel, which for CIC purposes may be a sub-millimeter diameter channel, for passage of regenerant water; and a second, suppression channel, which for CIC purposes may be a similar sub-millimeter diameter channel. An electrode, which is preferably partially insulated so as to direct an applied electrical current through an active zone within the block, is positioned in electrical communication with the eluent channel, and may be positioned like the electrode of the suppressor device. A counter electrode, which is preferably partially insulated so as to direct the applied electrical current through the active zone, is also positioned in electrical communication with the eluent channel, and may be positioned like the counter electrode of the suppressor device or within an active length of the eluent channel.

The disclosure presents a very low-volume, low-dispersion suppressor that provides sufficient suppression capacity for practical use without significant extra column broadening. An exemplary Nafion-based electrodialytic suppressor with <1 mm active suppression length connects directly to the end of a CIC separation column, and can suppress up to 100 mM NaOH at a flow rate of 100 nL/min with very low dispersion. Similar devices can alternately function as electrolytic eluent generators, producing up to 40 mM KOH eluent at about 450 nL/min for CIC applications and systems.

BRIEF DESCRIPTION OF THE DRAWINGS

FIG. 11A, 1.90 µL/min flow rate and 50 µA constant current; FIG. 11B, 1.89 µL/min flow rate and 100 µA constant current; FIG. 11C, 0.85 µL/min flow rate and 100 µA constant current; and FIG. 11D, 0.43 µL/min flow rate and 100 µA constant current.

DETAILED DESCRIPTION

Three exemplary designs of electrolytic capillary suppressors will be described, however the reader will appreciate that other designs, combining individual features from at least two of the designs while omitting one or more features from one or more designs, are contemplated. In general, the suppressor device comprises a monolithic block of ionomeric polymer material. The polymer material may be an ionomer such as Nafion perfluorosulfonate cation exchange resin (Du Pont Polymer Products Division, Wilmington, Del.), which can be obtained by boiling stock Nafion tubing of sufficiently large diameter and wall thickness in a solvent to remove contaminants and decomposition products. In a preferred preparation process, applicants first boiled Nafion material in 1:1 v/v dimethylsulfoxide:ethanol for 0.5 h to 1 h, and then boiled the solvent-boiled material in deionized water for 10-15 min, repeating the latter step multiple times to further remove decomposition products. Various ionomers may be used to provide cation suppression devices (Nafion and other cation exchange polymers) and anion suppression devices (POROS (Thermo Fisher Scientific, Waltham, Mass.) or other quaternary-aminated anion exchange polymers). The polymer material may alternately be a mixture including an ionomer, e.g., a block principally consisting of an ionomer but including other structural polymers, chemical stabilizers, and/or other polymeric and non-polymeric additives.

Figure 1A:
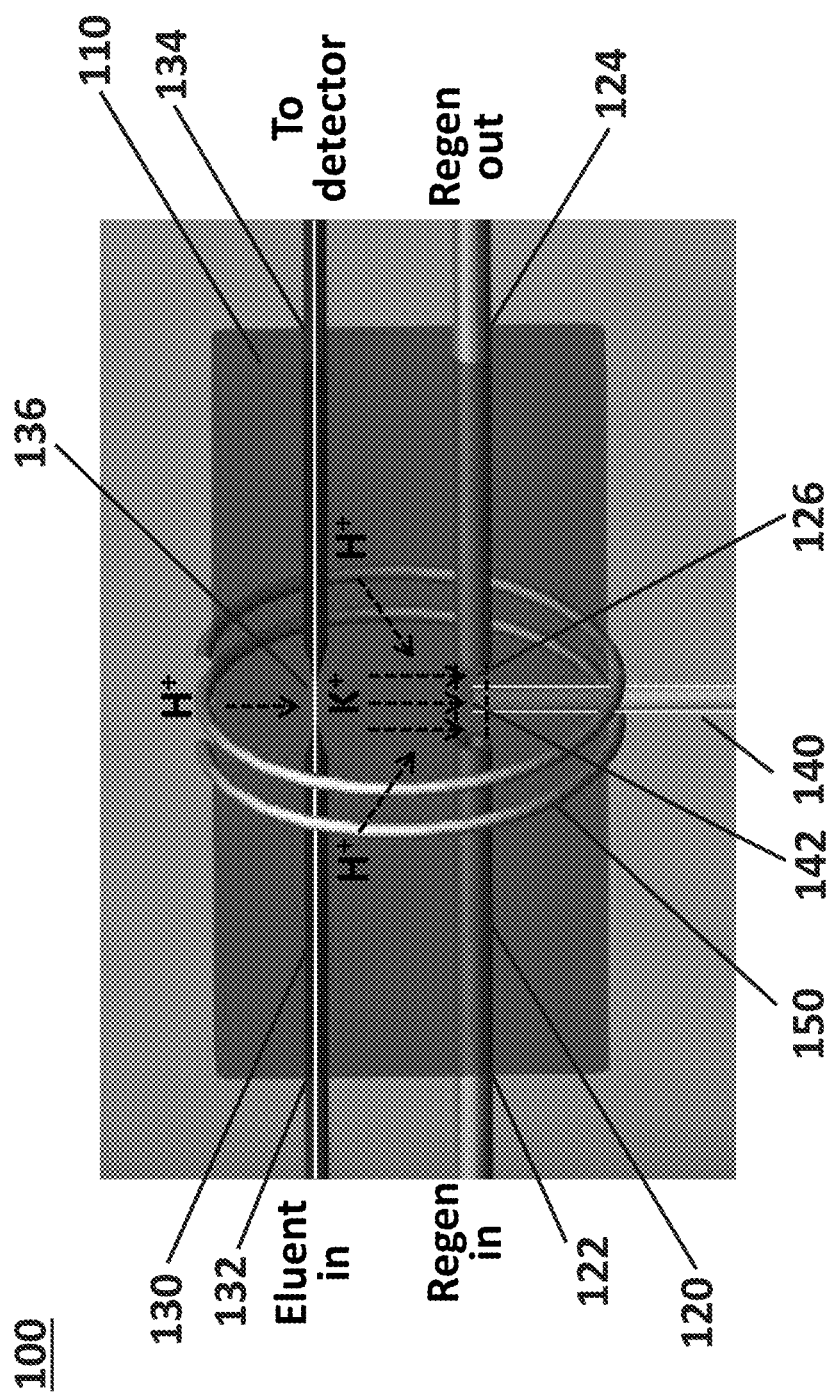
FIG. 1A is a schematic view of a first exemplary embodiment of a suppressor device.

In a first exemplary design 100, shown in FIG. 1A, the block of polymer material 110 includes a regenerant channel 120 and a suppression channel 130. The regenerant channel 120 is preferably a sub-millimeter diameter channel having an inlet port 122 and an outlet port 124, as well as an active length 126 of exposed polymer material. The regenerant channel 120 may be manufactured by any appropriate conventional process such as drilling, laser ablation, etc. In a preferred manufacturing process, a drill-and-ream process is used to form the channel 120 within the block 110. For example, the block 110 may be cooled to harden the material, a 0.35 mm drill bit may be used to drill through the block 110, and then the regenerant channel 120 may be enlarged with a 0.45 mm drill bit or reamer to remove any remnant material clinging to the wall of the channel. Applicants have found that a single step drilling process leaves more debris on the wall of the channel than a double step drilling process. The channel 120 itself may define a female inlet port 122 and outlet port 124. However, preferably, adapters or tubing may be inserted into both ends of the channel 120 to form external ports 122 and 124. For example, two PTFE tubes (0.3 mm i.d., 0.63 mm o.d.) may be inserted from the respective ends of the regenerant channel, leaving a gap of ~1 mm in the middle for the active length 126, and otherwise forming external ports 122 and 124. The suppression channel 130 is preferably a sub-millimeter, "micro diameter" channel, including an inlet port 132 and an outlet port 134 adjoining the respective ends of the channel, as well as an active length 136 of exposed polymer material. The suppression channel 130 may be manufactured by separating the polymer material along axis of the intended channel without removing polymer from the block 110. In a preferred manufacturing process, a stainless steel needle (0.3 mm diameter) may be pushed through the body of the block 110 along an axis that will serve as the eluent channel. The needle may be pulled out after a period of time (~10 min). In this process a physical channel can be microscopically observed at first, but that channel slowly collapses over time, essentially leaving a crack in the block 110 that constitutes the suppression channel 130. Ports 132 and 134 may be capillary tubes inserted into the block 110 at the respective ends of the channel. For example, two silica capillaries (25 μm i.d., 370 μm o.d, cut to ~100 mm in length) with honed ends (45°-60° taper to a pencil-like tip) may be inserted under microscopic guidance into the block 110 at the suppression channel 130, leaving a gap of 0.4-1.5 mm between the tapered tips for the active length 136. Another method of insertion may use solvent swelling of the block, which may be easier for no-leak insertion of soft plastic capillary columns into block 110 at the suppression channel 130. For example, the block 110 may be immersed in ethanol for 1 to 2 hours, capillaries and/or tubing inserted into the channels, and then immersed in boiling water for 10 minutes. The ethanol expands and softens the polymer material, while boiling in water drives out the ethanol, shrinking the polymer material around the inserted elements. For chromatographic systems, the terminus of the separation column may be inserted directly into the block 110 to form the inlet port 132. The inserted honed ends of the ports prise open the active length 136 to a rough-walled average diameter well below 100 μm, i.e., a "micro diameter." The reader will appreciate that while the disclosed dimensions are directed to a suppressor for CIC systems, the devices may be scaled or otherwise resized for use in larger-scale IC systems.

As shown, the regenerant channel 120 and suppression channel 130 are mutually parallel to one another. However, in other designs the channels may be mutually paraxial to one another, with the term "mutually paraxial" meaning being parallel to, or making a small angle with (+/−30 degrees) the longitudinal axis of one of the channels. See "paraxial," Random House® Dictionary Unabridged ("making a small angle with and lying close to the axis of an optical system"); "paraxial," American Heritage® Stedman's Medical Dictionary ("Located alongside of the axis of a body or part."). In still other designs, the regenerant channel 120 and suppressor channel might be orthogonal to one another. The channels 120 and 130 preferably sufficiently overlap to permit electrodialytic migration of ions between the active lengths 126 and 136. In general, the reader will appreciate that that the active length 126 of the regenerant channel 120 and the active length 136 of the suppression channel 130 should be disposed so that current flows across the suppression channel 130 and either across the regenerant channel 120 or within the regenerant channel 120, depending upon the positioning of electrodes 140 and 150 as discussed below.

A first at-least-partially exposed electrode 140 is positioned in electrical communication with the suppression channel 130. In the illustrated variation, an electrode 140 is positioned within the active length 126 of the regenerant channel 120. In other variations, an electrode 140 is positioned in contact with the block 110 at least on a side, relative to the regenerant channel 120, opposite to the suppression channel 130. The first electrode 140 may be, for example, a plate electrode disposed in contact with the surface of the block 110, a button electrode positioned adjacent the active length 126 in contact with the surface of the block 110, a wire electrode inserted into the block 110 in contact with the interior of the block, a wire electrode inserted into the block 110 and into the active length 126, or a wire electrode inserted via the regenerant channel 120 and into the active length 126. A second at-least-partially exposed electrode 150 is positioned in electrical communication with the suppression channel 130 across from the first electrode 140. In the illustrated variation, an electrode 150 is positioned in contact with the block 110 at least on a side, relative to the regenerant channel, opposite to the suppression channel 130. The second electrode 150 may be, for example, a plate electrode disposed in contact with an opposite surface of the block 110, a button electrode positioned adjacent the active length 136 in contact with an opposite surface of the block 110, a wire electrode inserted into the block 110 in contact with the interior of the block on a side (relative to the channel 130) opposite the channel 120, or even, as shown, a wire electrode wrapped around the exterior of the block 110. The electrodes are preferably partially insulated so as to direct current flow across the suppression channel 130 while reducing current flow from electrode 140 to electrode 150 through zones other than the active zone of the block 110. Preferably, at least 10 percent of the applied current should be directed across the suppression channel 130.

In the illustrated first design, the first at-least-partially exposed electrode 140 comprises a wire that extends into the block 110, with a non-insulated section or tip 142 positioned within the regenerant channel active length 126. For example, a 0.5 mm diameter wire may be insulated by coating the exterior with nail polish (except upon its tip) and inserted within the above-described, exemplary ~1 mm active length to serve as a cathode (anion chromatography application) or anode (cation chromatography application). The second at-least-partially exposed electrode 150 may comprise a bare wire wrapped around the outer surface of the block 110. For example, as otherwise shown, 1 to 2 turns of a 0.25 mm diameter noble metal wire may be wrapped around the block to function as an anode. In the first design, the exterior of the block 110 is maintained in a wetted condition to provide a conductive path between the non-insulated tip 142 and the second wire 150. The wire may be a typical electrode material such as platinum, stainless steel, or other known material, but should be relatively inert so as to be suitable for use in chromatography applications. When used as anode, the wire must be made of a metal that will not be electrochemically corroded, and platinum or platinum coated wires are suitable.

Figure 1B:
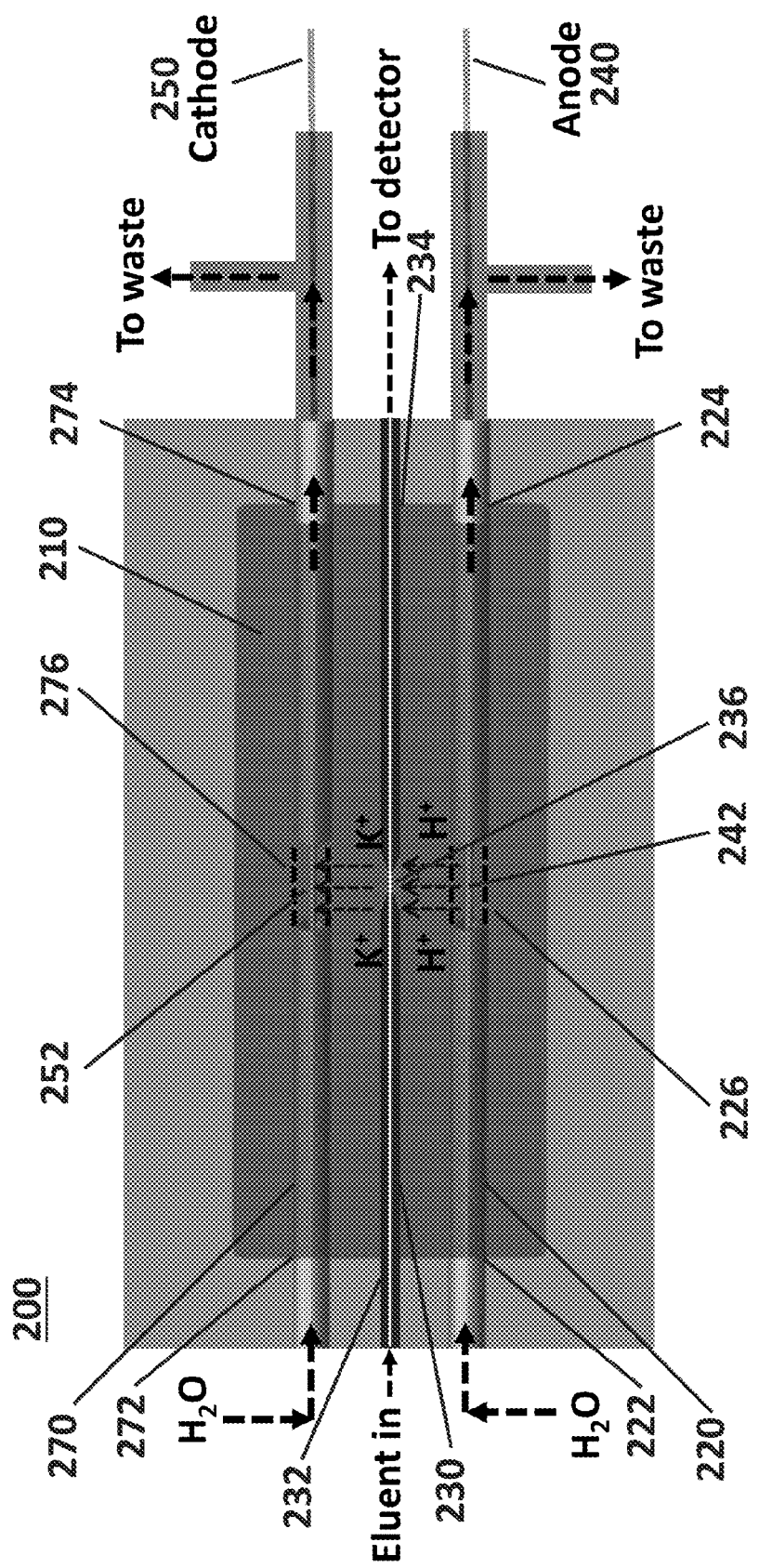
FIG. 1B is a schematic view of a second exemplary embodiment of a suppressor device.

In a second exemplary design 200, shown in FIG. 1B, the block of polymer material 210 includes a first regenerant channel 220, a suppression channel 230, and a second regenerant channel 270. The first and second regenerant channels 220, 270 may be provided, and be manufactured, as otherwise described in the first design, with corresponding inlet ports 222, 272, outlet ports 224, 274, and active lengths 226, 276. The suppression channel 230, along with inlet port 232 and outlet port 234, may also be provided and manufactured as described in the first design. All three channels 220, 230, and 270 may be mutually parallel, mutually paraxial, or otherwise sufficiently overlap to permit electrodialytic migration of ions between the active lengths 226, 236, and 276. Again, the active lengths 226, 236, and 276 of the respective channels 220, 230, and 270 should be disposed so that current flows across the suppression channel 230 and either across the regenerant channels or into/from the regenerant channels, depending upon the positioning of electrodes 240 and 250.

The illustrated second design 200 otherwise differs in its electrode configuration. A first at-least partially exposed electrode 240 having a non-insulated section or tip 242 extends from the inlet port 222 or outlet port 224 to at least the active length 226, with the section or tip 242 positioned within the regenerant channel active length 226. For example, a 0.1 mm diameter platinum wire may be inserted to a depth extending to at least the active length 226 of the regenerant channel 220, with the opposite end of the wire exiting the regenerant stream via a partially sealed-off, T-arm tubing union, and tubes joined to the open T-arms serving as the inlet or outlet for the regenerant stream directed through the regenerant channel. In another variation of positioning of the second at-least partially exposed electrode, an electrode 250 is positioned within the active length 276 of the second regenerant channel 270. For example, a second at-least partially exposed electrode 250 having a non-insulated section or tip 252 extends from the inlet port 272 or outlet port 274 at least to the active length 276, with the section or tip 252 positioned within the other regenerant channel active length 276 and the applied electric field running across the active length 236 of the suppression channel 230. The applied current consequently flows within the first regenerant channel 220, from or into the channel depending upon whether the electrode 240 functions as an anode or a cathode, across the suppression channel 230, and within the second regenerant channel 270. It will be appreciated that in the second exemplary design the second or counter electrode 250 is positioned within an active length 276 of an optional (with respect to the first exemplary design) third channel 270 positioned on a side, relative to the suppression channel 230, opposite to the first regenerant channel 220.

Figure 1C:
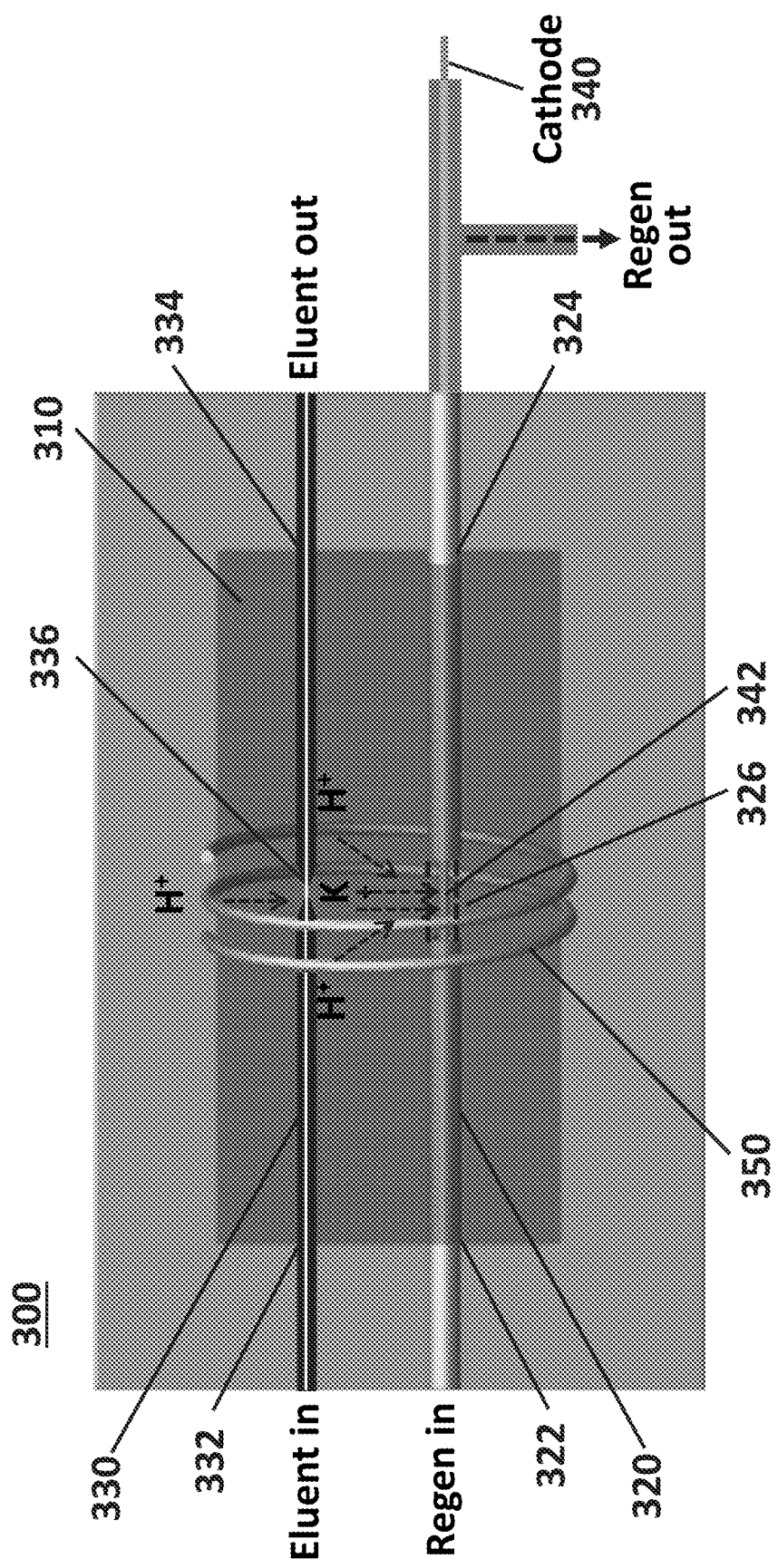
FIG. 1C is a schematic view of a third exemplary embodiment of a suppressor device.

A third, exemplary design 300, shown in FIG. 1C, can be thought of as a hybrid of the first 100 and second 200 designs. A block of polymer material 310, like the block 110, includes a regenerant channel 320 and a suppression channel 330. The regenerant channel 320 may be provided, and be manufactured, as described in the first design, with corresponding inlet ports 322, outlet ports 324, and active length 326. The suppression channel 330, along with inlet port 332 and outlet port 334, may also be provided and manufactured as described in the first design.

However, the illustrated third design 300 has an electrode configuration combining aspects of the configurations present in the first and second illustrated designs. A first at-least-partially exposed wire 340 having a non-insulated section or tip 342 extends from the inlet port 322 or outlet port 324 at least to the active length 326, with the section or tip 342 positioned within the regenerant channel active length 326 so as to serve as an electrode. A second at least partially exposed wire 350 is positioned on the outer surface of the block 310 so as to serve as a counter electrode. Again, for example, 1 to 2 turns of a 0.25 mm diameter wire may be wrapped around the block to function as the anode (anion chromatography application) or cathode (cation chromatography application). It will be appreciated that even if electrode 350 is a bare wire wrapped around the outer surface of the block 110, current will flow across the suppression channel 330 and cause an electrodialytic migration of ions from the suppression channel, although not with the sort of efficiency achievable by using a wire having a non-insulated section exposed only on a side of the suppression channel 330 opposite the wire 340, or one of the other electrode variants described above.

EXAMPLES

Suppression Capacity Measurement of an Exemplary Suppressor.

Figure 1D:
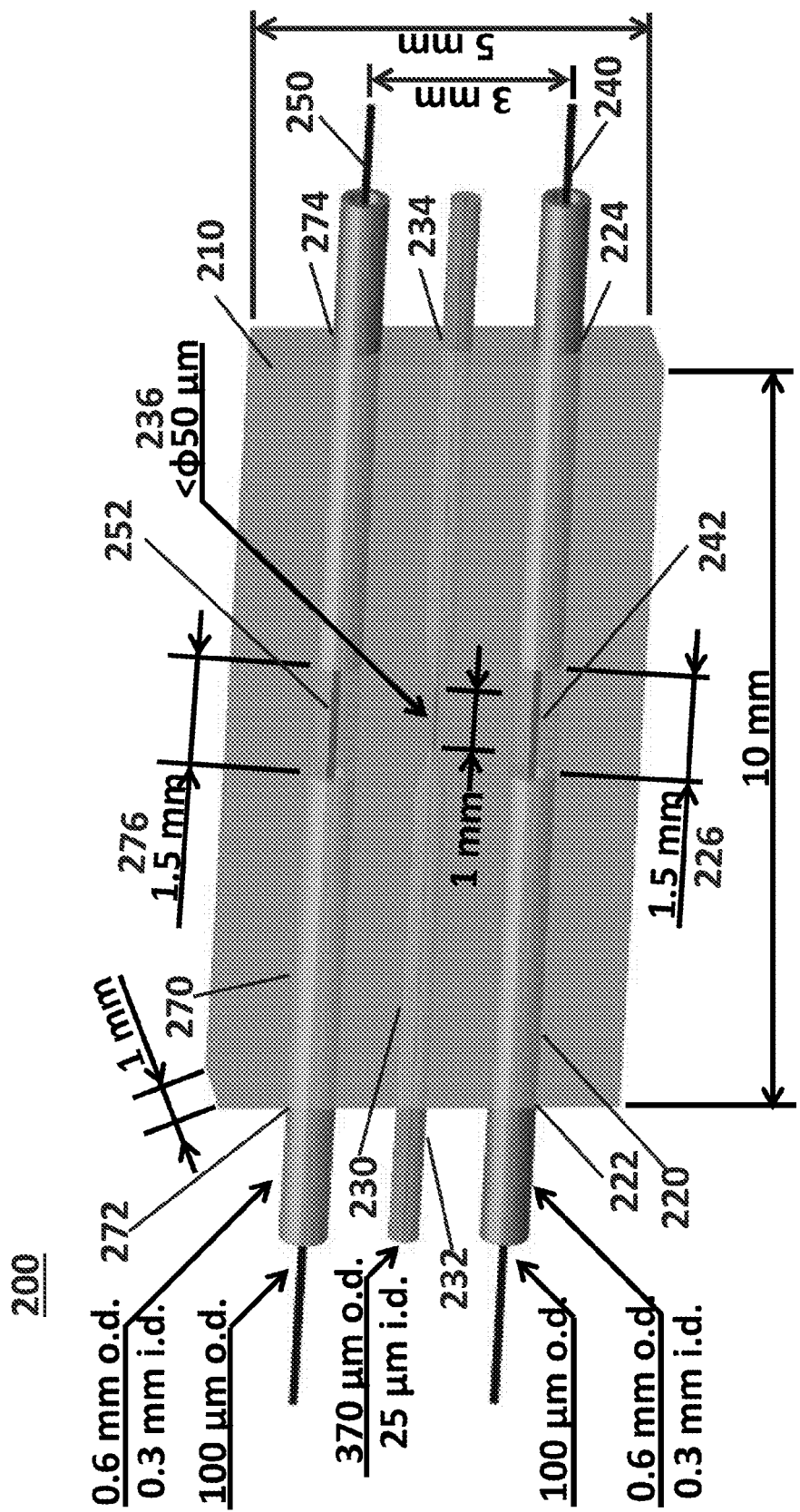
FIG. 1D is a dimensional schematic of the second exemplary embodiment, illustrating exemplary sizing and spacing for elements of the device.
Figure 2:
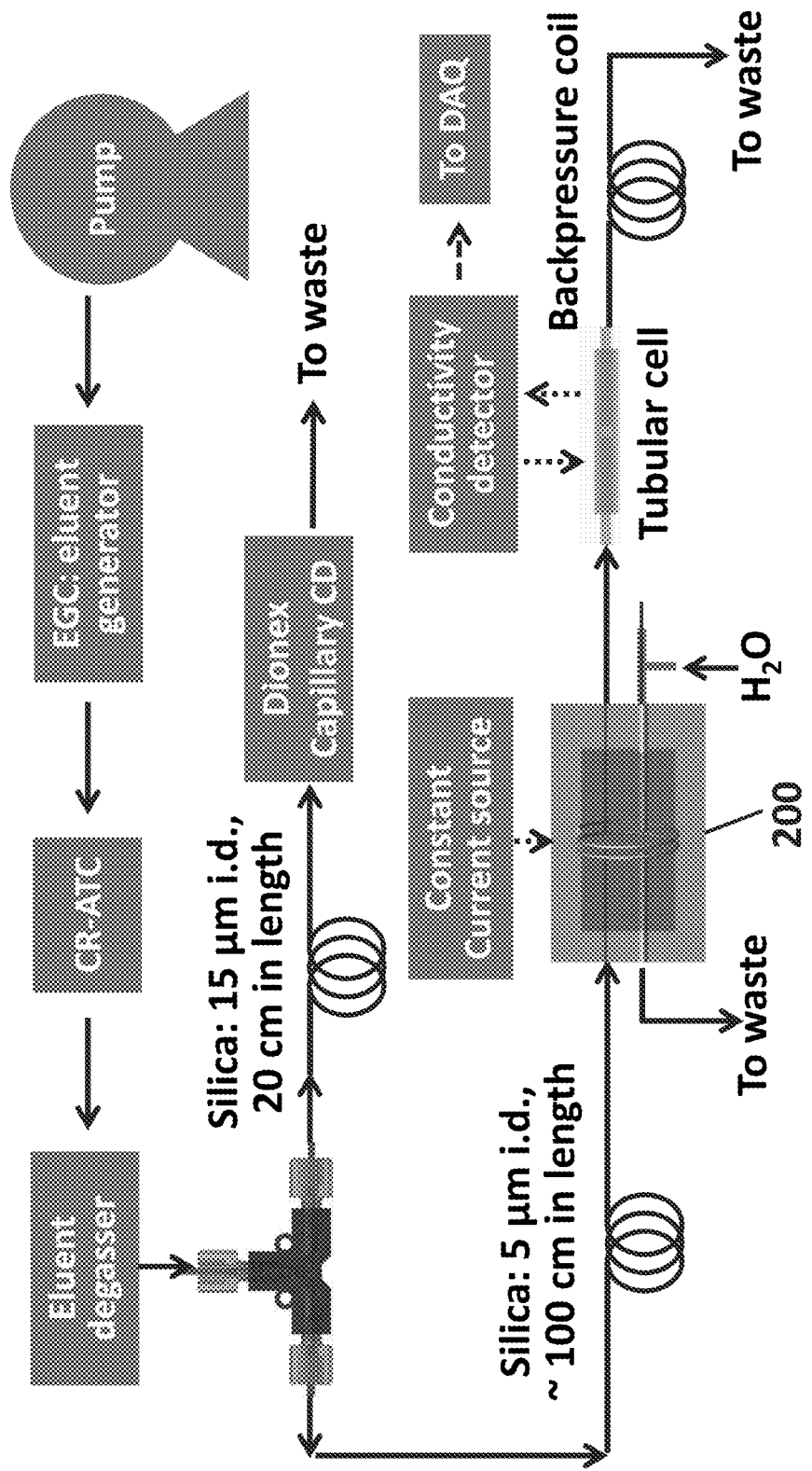
FIG. 2 is a schematic view of an exemplary SCCIC system
Figure 5:
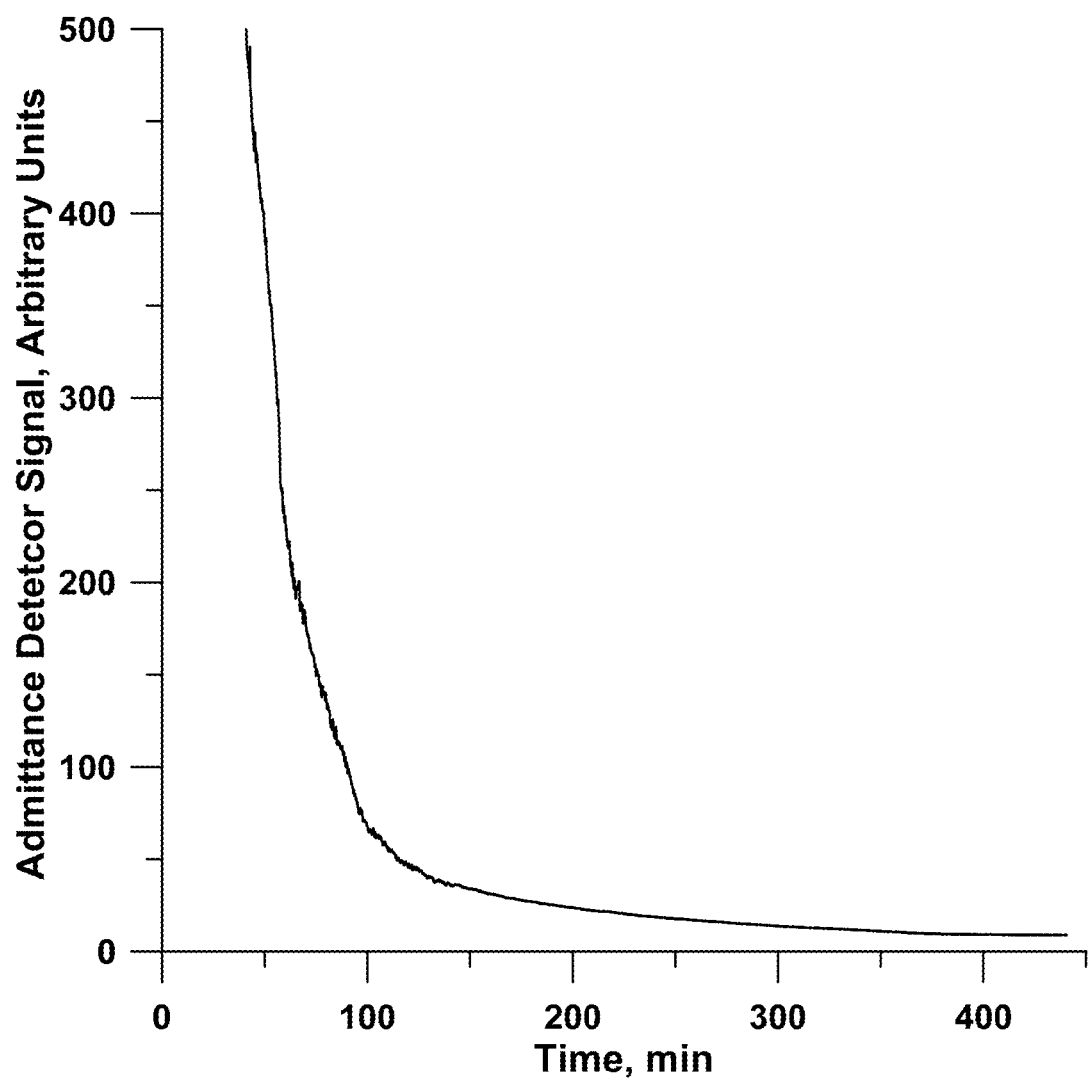
FIG. 5 is a plot of suppression capacity for the CIC-scale suppressor shown in FIG. 1D (actual active suppression length of 1.08 mm) in the system shown in FIG. 3. Conditions included a ~92 mM NaOH eluent delivered at 95 nL/min, an applied suppression current of 40 µA through the electrodes, and detection via a TraceDec detector operated at 38 kHz, offset, 0, positioned 30 mm from the center of the suppressor device using a 25 µm diameter exit capillary.

FIG. 2 shows a capillary IC system (ICS-5000, www.dionex.com) with a LiOH eluent generator that was used to measure the suppression capacity of a design 200 configured according to the exemplary dimensional specifications provided in FIG. 1D. LiOH was chosen as the worst case eluent among alkali hydroxides, because as the electrical mobilities of the respective cations increases, so does the suppression capacity (LiOH<NaOH<KOH). The suppressor was designed to operate at a flow <100 nL/min while the minimum flow rate that the pumping system could reliably provide was 1.0 µL/min. Thus, the pumped flow from the eluent generator was split by a tee with different capillary restrictors placed on each arm. Initial split estimates were made by the Hagen-Poiseuille equation [17], and exact values subsequently determined by a nano flow sensor (http://www.westernanalytical.com/pdf/Nanoflow%20Sensor.pdf) or collection and gravimetry. A homemade conductivity cell was constructed with two small segments of 100 µm i.d., 175 µm o.d. stainless steel tubes that were inserted in a glass capillary, epoxied in place with a ~0.3 mm gap between them, and silver epoxied to lead wires. The conductivity of the suppressor effluent was measured with a Dionex CDM-1 conductivity detector, with the cell and detector combination calibrated with 1.0 mM KCl. Results are plotted in FIG. 5. As shown, it may take several hours after first startup for residual ionic contaminants to be completely removed from the block device, but equilibration becomes considerably faster on subsequent use. Of course consumption of energy and consumables are so low that there is no reason to shut down such a system after initial setup.

Suppressed CIC System.

Figure 3:
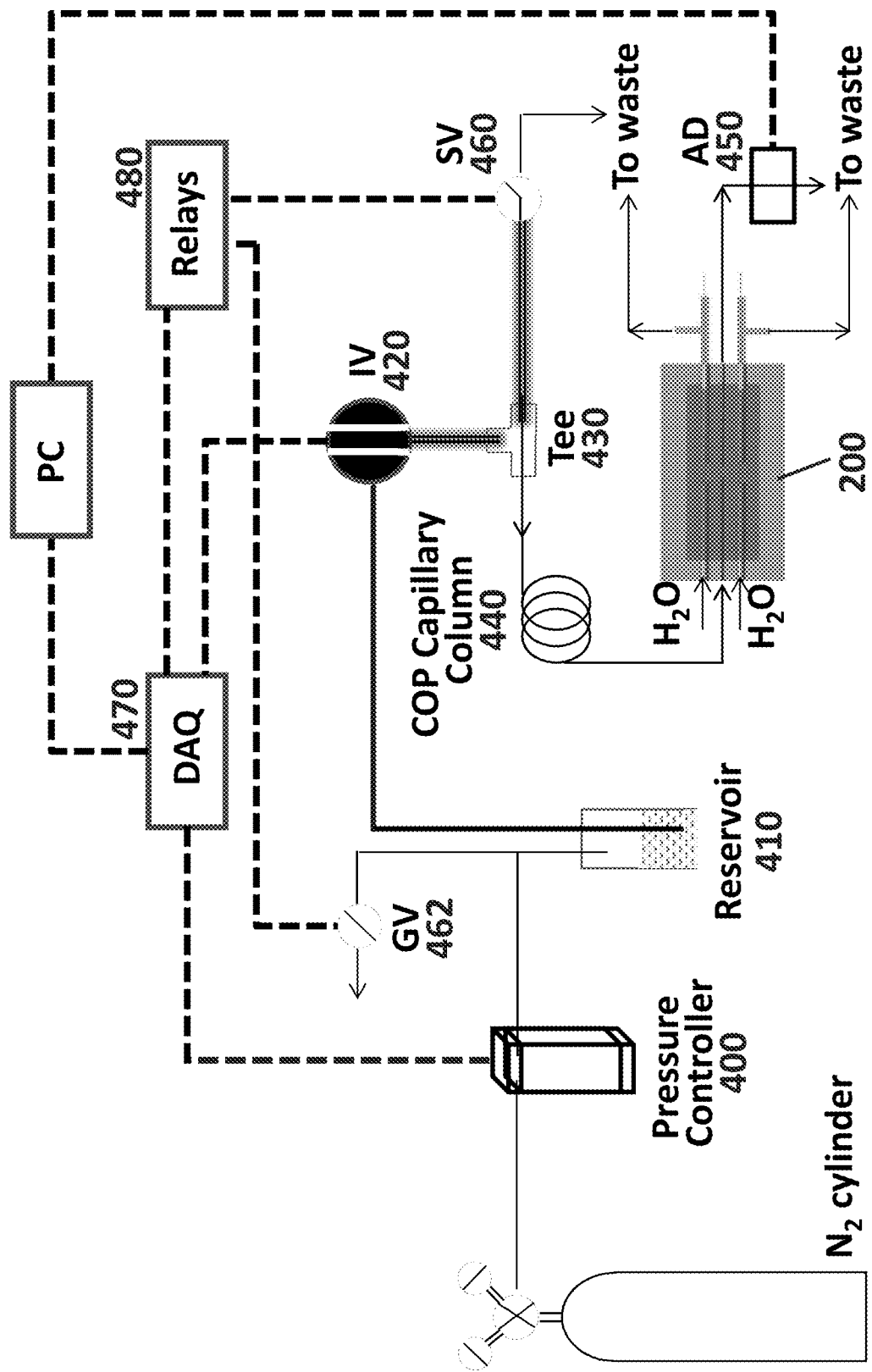
FIG. 3 is a schematic view of the SCCIC system used in the working examples.
Figure 4:
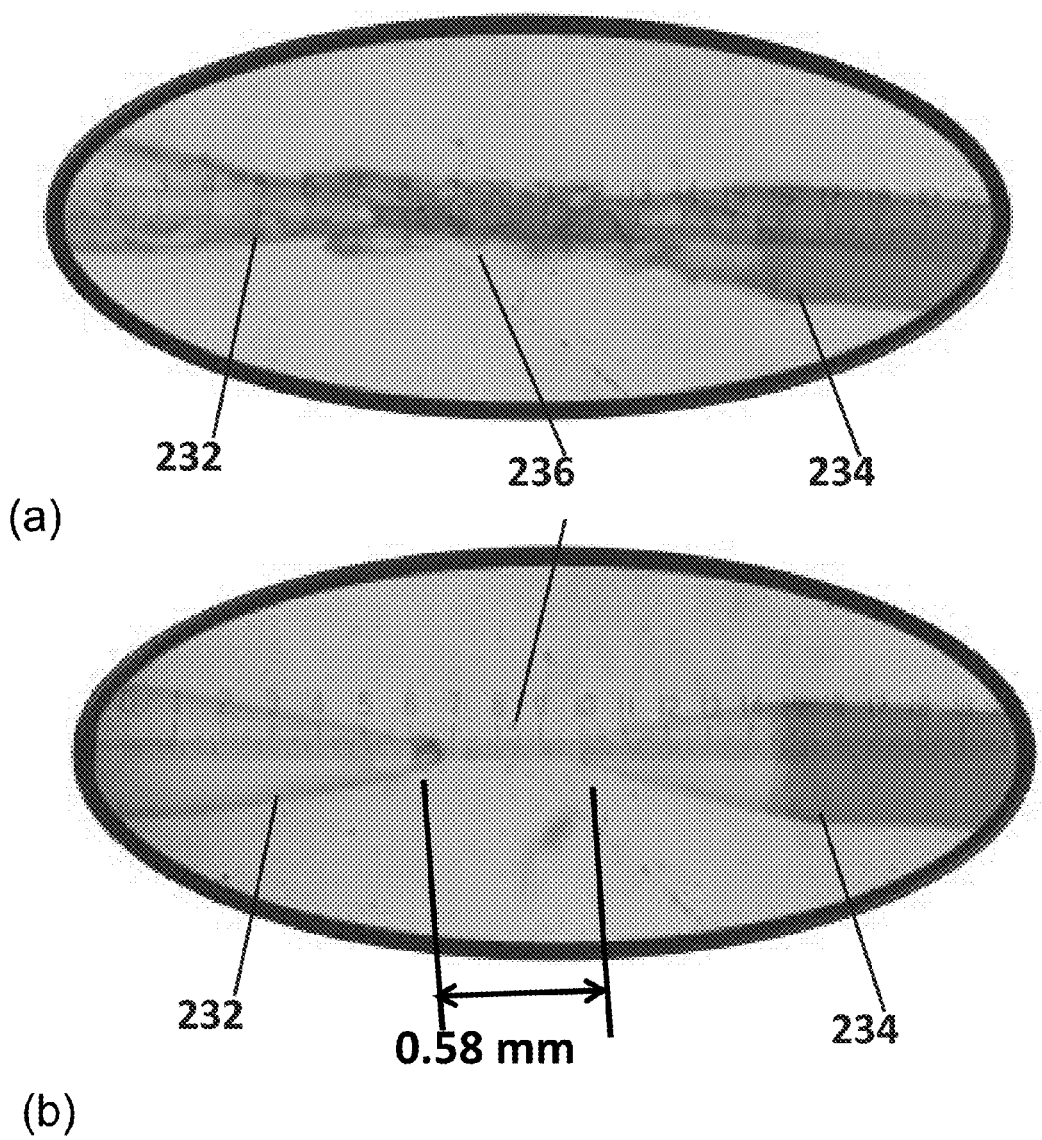
FIG. 4 is a photograph of a suppression channel of a CIC-scale implementation of the device illustrated in FIG. 1B, centered upon the active suppression length, in (a) a dry state (showing the roughness of the suppression channel wall) and (b) a wet state (where, because the refractive index of wetted Nafion material is very close to that of an aqueous solution, the roughness of the suppression channel wall is not visible).

FIG. 3 shows an exemplary SCCIC system used for the remaining examples. The system includes a pressure controller 400 (14-100 psi, P/N 990-005123-100, http://ph.parker.com/us/12051/en/oem-epminiature-pressure-controller), a reservoir 410 (in-house machined Plexiglas), an injection valve (IV) 420 (six-port electromechanical, www.vici.com), a "zero dead volume" tee 430 (www.vici.com), a separation column 440 (~740 mm long AS18 latex coated 28 µm i.d. sulfonated COP column; where AS18 latex is a latex modified to have alkanol quaternary ammonium groups), and a variable frequency admittance detector (AD) 450 (two were used interchangeably: TraceDec, www.istech.at, 38-620 kHz; Analytical Foundry (AF), www.analyticalfoundry.com, 0.1-100 kHz, but only the latter detector could be used for suppressed measurements). Two solenoid valves, SV 460 and GV 462 (SV, 100 psi, P/N HP648T031; GV, 150 psi, Skinner P/N MBD002) were configured for the introduction of picoliter (pL) to nanoliter (nL) volume samples (by automated time-pressure based hydrodynamic injection) and for automation of the chromatography runs. The system was controlled by a laptop computer (PC) connected to a data acquisition/digital I/O device (DAQ) 470 (model no. USB-1408FS, www.mccdaq.com), the latter, in turn, controlling a set of relays 480 for operation of the IV 420, SV 460, and GV 462. Eluent was pressurized by $N_2$ (as regulated from the pressure controller) and delivered through IV 420 into the tee 430. µL-scale samples were loaded into the IV loop and the IV 420 was then switched into the injection mode while the SV 460 was briefly opened for a precise time (typ.<1 s) to allow the middle of the sample to arrive at the tee undiluted. SV 460 was then closed for a predetermined period to drive a small volume (pL to nL) to enter the separation column 440. Next, SV 460 was opened for several seconds to flush the remaining sample in the tee and the downstream line to SV 460. Finally, SV 460 was closed, and chromatographic separation began. Further operational details can be found in a prior publication [18], which is hereby incorporated by reference in its entirety. Labview program summaries for controlling the system to measure the column capacity and run chromatography are shown in Table 1.

detector. In the disclosed devices, dispersion between the column and the suppressor can be avoided by configuring the separation column to terminate within the block, adjoining the suppression channel, so as to form an inlet port. The outlet port capillary tube (15 to 25 µm i.d. fused silica), functioning as the detection capillary, can also be configured to terminate within the block, adjoining the suppression channel, so as to form an outlet port. With the terminus of the separation column within the block configured to be ≤1.5 mm away from the terminus of the detection capillary, a mechanically opened, exposed portion of the suppression channel defines the suppressor channel active region. The arrangement prevents the suppression channel from completely closing up while maintaining a "micro diameter" [(<100 µm, preferably <50 µm) opening within the channel. In the exemplary system, the edge of the conductivity detector head was kept ≤50 mm from the suppressor block. Although the inner surface of the suppression channel is not smooth, as can be seen in the top panel of FIG. 4; this lack of smoothness may actually be helpful by breaking up laminar flow and promoting mass transfer. With the first and third exemplary designs 100, 300, the suppressor must be immersed in an aqueous solution to provide a conductive path between electrodes. However, even with the second exemplary design 200, dimensional changes may occur if portions of the suppressor block become dry, so it is recommended that that suppressor device 200 also be immersed in an aqueous solution. With some devices, applicants have observed a slow increase in backpressure and, in an extreme case with longer active suppression lengths, complete blockage of the suppression channel over time. This could be prevented by incorporating a small amount (5-10%) of a swelling solvent (e.g., ethanol or methanol) into the aqueous immersion solution.

TABLE 1

SCCIC program sequence for sample injection and separation, one cycle.

| Step | Duration time | SV | GV | IV | Pressure | Comment |
|---|---|---|---|---|---|---|
| 1 | 1 s | off | off | load | 15 | System initialization; apply pressure to the system; sample has been loaded in injection valve before running the program |
| 2 | 1 s | off | off | injection | 15 | Switch injection valve to make the sample loop to connect the eluent line |
| 3 | 350 ms | on | off | injection | 15 | Open SV to move the undiluted sample zone to the Tee |
| 4 | 100-5000 ms | off | off | injection | 15 | Close SV for introducing sample into the capillary column |
| 5 | 3-4 s | on | off | injection | 15 | Open SV again for cleaning the remaining sample in the Tee and the line |
| 6 | 1 s | off | off | injection | 45 | Close SV and increase the pressure to begin the separation; trigger data acquisition |
| 7 | $t_{sep}$ | off | off | injection | 45 | Separation step. The time duration depends on the needed separation time plus any column equilibration time needed in gradient elution |
| 8 | 1 s | off | off | load | 45 | Switch IV back to load position |
| 9 | 3-15 s | off | on | load | 0 | Open GV to release pressure |
| 10 | 1 s | off | off | load | 15 | Return to the initial status for next cycle |

In single column (NSIC) mode, the applicants have observed separation column efficiencies of up to 150,000/m on 19 µm diameter poly(methylmethacrylate) columns [18]. High efficiencies have also been observed with similar COP columns [16]. However, such efficiencies have not been attainable when using tubular ion exchange suppressors based upon the smallest diameter ion exchange tubing accessible to the applicants, similar to those used previously [12, 19], due to dispersion in (a) the connections, (b) the suppressor itself, (c) the additional length of tubing added to place the Mass Transfer Considerations in the Absence of an Electric Field.

In any membrane based process, transport to and then through the membrane are serial processes, and either one can be rate-limiting. However, with the assumption that transmembrane transport is not limiting, i.e., the membrane wall acts as a perfect sink, it is possible to compute the active suppression lengths needed to remove specified fractions of the eluent ions (cations or anions, depending upon application) for a cylindrical channel under laminar flow conditions (assumes ion transport is diffusion limited). The Gormley-Kennedy equation applies—although it is an infinite series, in the present case, a one-term approximation is adequate:

$$1-f = 0.81905 e^{-3.6568\mu} \quad \text{Equation (1)}$$

Where f is the fraction removed, and $\mu$ is a dimensionless parameter given by:

$$\mu = \frac{\pi D L}{Q} \quad \text{Equation (2)}$$

where D denotes the diffusion coefficient, L the length of the tube, and Q is the volumetric flow rate in compatible units.

From the known diffusion coefficients of $K^+$, $Na^+$, or $Li^+$, the required passage length L to achieve f=0.9999 at a specific flow rate Q can be readily calculated, and such calculation results are listed in Table 2. At a flow rate of 100 nL/min to achieve 99.99% removal the minimum passage lengths for $K^+$, $Na^+$, and $Li^+$ are computed to be 0.67, 0.98, and 1.27 mm, respectively. However, this is the most restrictive condition; there are a variety of reasons (e.g., non-circular channel with non-smooth walls, finite length for laminar flow development, etc.) that mass transfer to the wall should be more efficient than computed from Equation (1). In any case, an active suppression length of about 1 mm would be adequate for flow rates ≤100 nL/min.

TABLE 2

Calculated required passage length in capillary suppressor under different flow rates for 99.99% removal (f = 0.9999)

| Q (µL/min) | $L_{K+}$ (mm) | $L_{Na+}$ (mm) | $L_{Li+}$ (mm) |
|---|---|---|---|
| 1 | 6.7 | 9.79 | 12.73 |
| 0.9 | 6.03 | 8.81 | 11.45 |
| 0.8 | 5.36 | 7.83 | 10.18 |
| 0.7 | 4.69 | 6.85 | 8.91 |
| 0.6 | 4.02 | 5.87 | 7.64 |
| 0.5 | 3.35 | 4.89 | 6.36 |
| 0.4 | 2.68 | 3.92 | 5.09 |
| 0.3 | 2.01 | 2.94 | 3.82 |
| 0.2 | 1.34 | 1.96 | 2.55 |
| 0.1 | 0.67 | 0.98 | 1.27 |
| 0.09 | 0.6 | 0.88 | 1.15 |
| 0.08 | 0.54 | 0.78 | 1.02 |
| 0.07 | 0.47 | 0.69 | 0.89 |
| 0.06 | 0.4 | 0.59 | 0.76 |
| 0.05 | 0.33 | 0.49 | 0.64 |
| 0.04 | 0.27 | 0.39 | 0.51 |
| 0.03 | 0.2 | 0.29 | 0.38 |
| 0.02 | 0.13 | 0.2 | 0.25 |
| 0.01 | 0.07 | 0.1 | 0.13 |

Mass Transfer Considerations in an Electrodialytic Capillary Suppressor.

Many macroscale dual membrane electrodialytic suppressors can be operated with either chemical or electrodialytic regeneration. In the electrodialytic configuration, only one membrane (or one wall of a device) is effective for alkali cation transport out. However, the transport rate in the presence of an electric field increases more than enough to offset this: for the same suppressor, dynamic ion exchange capacities are invariably greater in the electrodialytic configuration.

In the second exemplary design 200, a preferred electrode separation is 3 mm with an applied voltage difference ranging from 3.6 to 20 V, depending on the eluent concentration suppressed and the anode solution composition. The applied voltage difference is dissipated over, beginning from the anode in an exemplary device, (a) ~150 µm of water, (b) ~1.5 mm of Nafion, (c) ~35-40 µm (based on microscopic observation) of eluent channel that ranges in composition along its length from the unsuppressed eluent to pure water, (d) ~1.5 mm of Nafion and (e) 150 µm of an alkali hydroxide, generated from suppression. Of these, (b), (d), and (e) are expected to be highly conductive and do not contribute much to voltage drop across the electrodes. Thus if the 150 µm regenerant water channel and the 35 to 40 µm suppression channel, both assumedly filled with pure water, are the primary voltage drop locations, the field strength in the eluent channel will minimally be ~19 kV/m. As an approximation, if one assumes that the suppression channel is cylindrical, a 35 to 40 µm diameter channel has a volume of 0.96-1.25 nL/mm length, and the mean residence time for a flow rate of 100 nL/min (1.67 nL/s) is 570-750 milliseconds/mm. Given the ionic mobilities of $K^+$, $Na^+$, $Li^+$ as 7.6×, 5.2×, 4.0×10$^{-8}$ m$^2 \cdot$s$^{-1} \cdot$V$^{-1}$, the respective velocities at 1.9×10$^4$ V/m are respectively 1440, 990, and 760 µm/s, thus respectively requiring 24.3(27.8), 35.4(40.4) and 46.0(52.6) milliseconds to traverse the entire width of a 35(40) µm channel. The necessary active suppression lengths for $K^+$, $Na^+$, $Li^+$ will all be below 0.1 mm. The suppressor channel is not however, filled with pure water and the field across the eluent channel is thus overestimated, requiring greater suppression lengths in practice. On the other hand, the voltage drop across the anode channel can be dramatically reduced by using a dilute acid instead of water, less applied voltage is required to accomplish the same degree of suppression by reducing the drop in the anode channel and with an attendant increase in current efficiency. For example, in an implementation of the second exemplary design 200 (0.69 mm active suppression length), when supplying pure water to the anode channel 220 and applying a 30 µA constant current to the device, a voltage drop of 4.7-5.1 V across the anode and cathode was observed. To fully suppress 50 mM NaOH at 160 nL/min, a constant current of 35 µA was needed, corresponding to a current efficiency of 37%. When supplying ~5 mM $H_2SO_4$ to the anode channel 220 and applying a 30 µA constant current to the device, the voltage drop decreased to 3.3-3.5 V. To fully suppress 50 mM NaOH at 199 nL/min, a constant current of 20 µA was sufficient, translating to a current efficiency of up to 80%.

Electrolytic Current Efficiency.

Because current can flow through the suppressor block around the suppression channel, current efficiency will necessarily be less than unity. For the exemplary results plotted in FIG. 5, 0.14 neq/s $Na^+$ eluent is being removed/suppressed by transport from the suppression channel 230 into the regenerant channel 220 of the second exemplary design 200, the theoretical current requirement thus being 13.6 µA. In practice, 40 µA was required to achieve suppression, corresponding to a current efficiency of 34%. As a benchmark, to suppress 100 mM KOH at 10 µL/min the recommended current for a commercial packed capillary suppressor (ACES 3000 capillary suppressor) for use with a 400 µm diameter packed columns is 15 mA, which would represent a current efficiency of 11%. At lower concentrations, the recommended currents in this commercial device represent even lower current efficiencies. Current efficiencies in the present suppressor can be improved and power dissipation/Joule heating reduced with a small concentration of acid in the anode channel as mentioned above.

Suppressor Designs and Performance.

Both the first and third exemplary designs 100, 300 can successfully suppress hydroxide eluents at least up to 20 mM concentration. The current efficiency of these suppressors are, however, much lower than that of the second exemplary design 200, which focuses the field better on the active length 236 of the suppression channel 230. With the first exemplary design 100, cooling of the cathode (section or tip 142) is especially inefficient; long-term operation at higher currents can even result in burning around the cathode and burnt polymer particles can accumulate on the surface of the cathode, eventually deteriorating function and performance. With the system setup shown in FIG. 3, the second exemplary design 200, with an active suppression length of 1.08 mm, can suppress 100 mM NaOH at a flow rate of 100 nL/min using an applied constant current of 40 µA.

Suppressed vs. Nonsuppressed Chromatograms—Suppressor Induced Dispersion.

Figure 6:
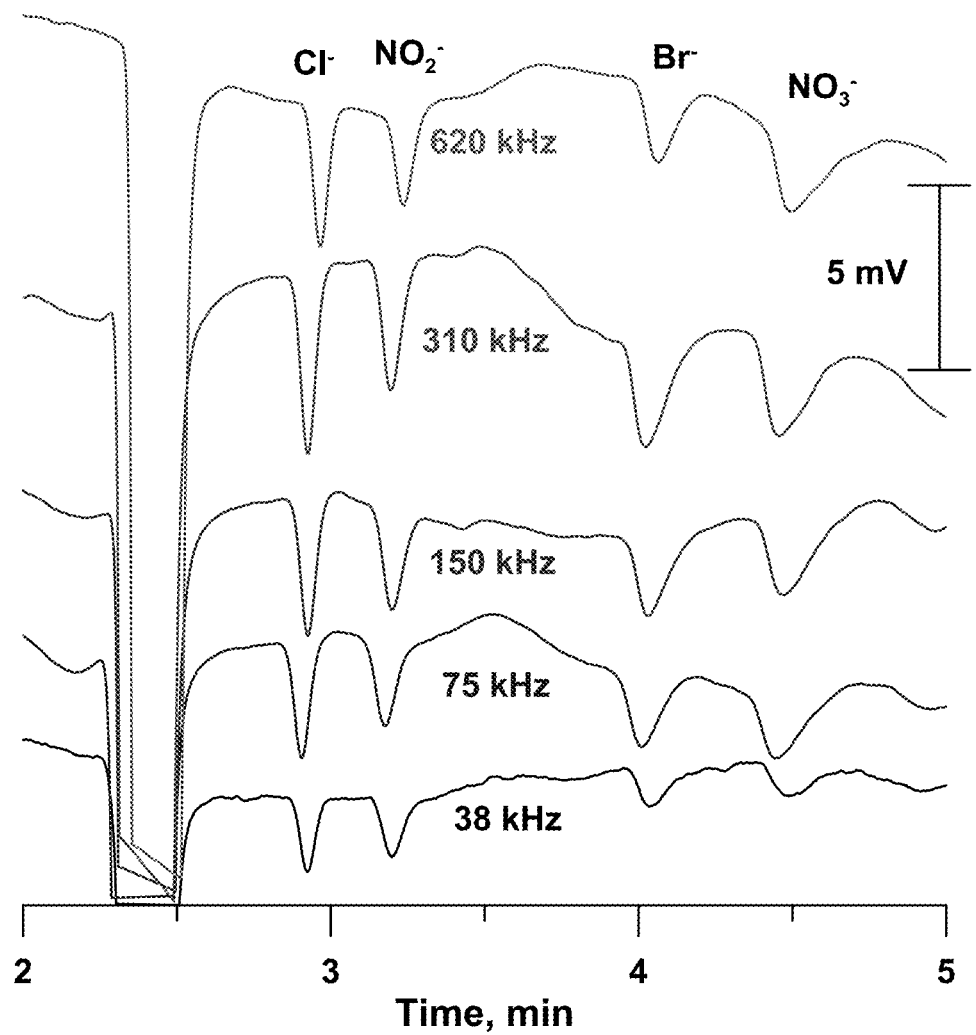
FIG. 6 is a plot of overlain chromatograms obtained without suppression via a TraceDec detector (where, for each chromatogram, displacement towards the illustrated time axis represents a change in relative admittance, scaled as shown at the upper right), run at different operating frequencies for each otherwise identical run, in the system shown in FIG. 3.

Dispersion induced by any given chromatographic device is typically determined as:

$$\sqrt{W_{1/2}^2 - W_{1/2}^2}$$  Equation (3)

where $W_{1/2}$ and $W_{1/2}$ are respectively the half widths of a peak with and without the device under consideration incorporated in the system, respectively [21]. The underlying assumptions are that the response behavior, both in regard to intrinsic response characteristics of the property monitored (here, putatively "conductivity" as a function of concentration) is linear and the detector is able to faithfully monitor the measured property (for example, at high absorbance values, stray light limitations of a detector may compromise the ability to measure the true absorbance). In the present case, neither one of these two criteria are strictly met. In nonsuppressed detection, the concentration of the electrolyte is in a domain where it changes less than linearly with concentration (cf. the Onsager equation [22]). Second, "contactless conductivity" detectors do not really measure the conductivity, they measure the overall impedance between the detector electrodes, i.e., they are really admittance detectors [23]. Depending on the background conductivity, both the response and the linearity of the response with concentration changes with the probe frequency, also affecting the apparent efficiency/half-width of the peak as illustrated in FIG. 6. In the present case, if one measures the half-widths/peak efficiencies before (nonsuppressed mode) and after the suppressor (suppressed mode) simultaneously (with detectors operating at frequencies optimized for each conductance range), the solution will necessarily have traveled through an additional length of column/tubing (aside from the suppressor) between the first and the second detectors. This will result in an increase both in the apparent retention time and the measured dispersion, due to the entire additional transit and not from the suppressor alone.

Figure 7:
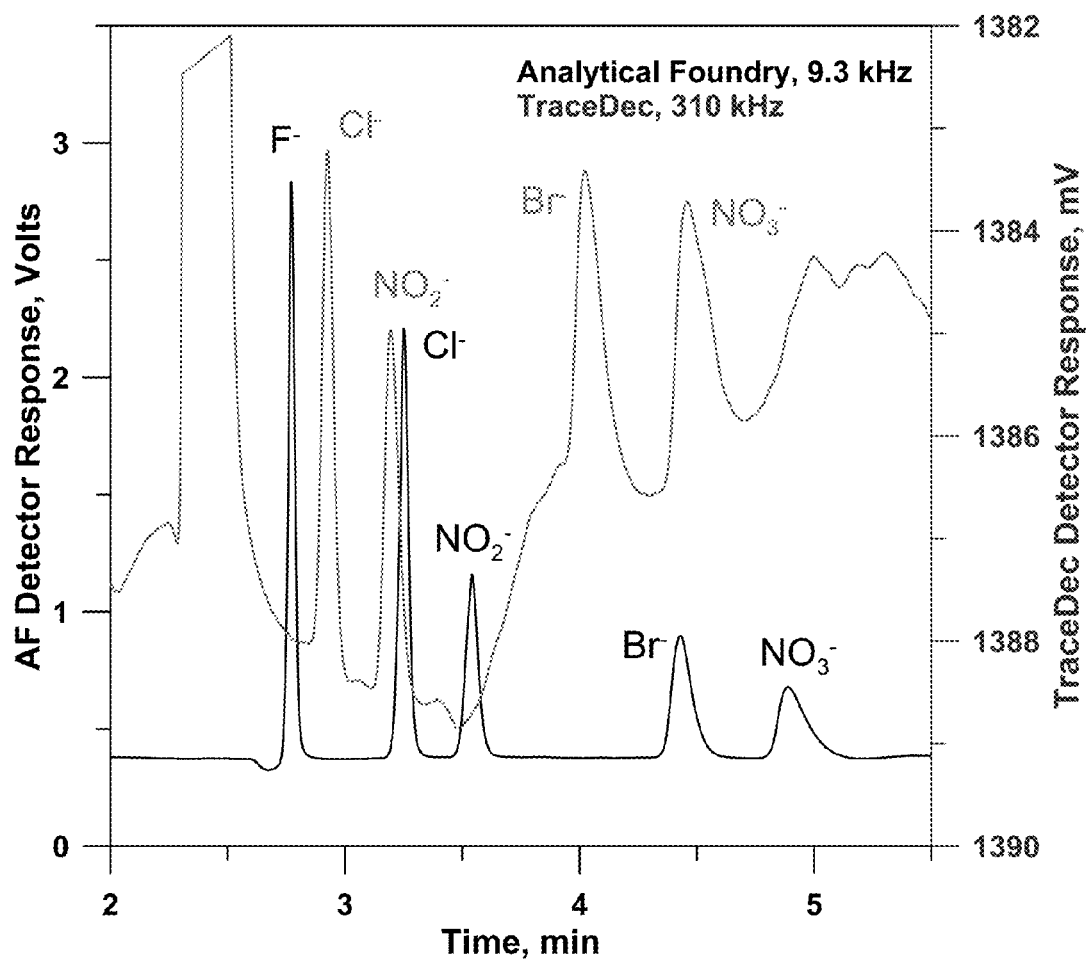
FIG. 7 is a comparative plot of chromatograms obtained without (top trace) and with (bottom trace) suppression (0.45 mm active suppression length) for an analyte mixture containing 100 µM concentrations of each of the 5 common anions, injection volume of 6.8 nL, separated using an 8.0 mM electrogenerated LiOH eluent at a flow rate of 170 nL/min. The post-suppression detector signal (bottom trace) was acquired by an Analytical Foundry (AF) detector operated at 9.3 kHz (left vertical axis), while the unsuppressed/pre-suppression detector signal (top trace) was acquired by a TraceDec detector operated at 310 kHz (right vertical axis) placed 50 mm before the end of the separation column.
Figure 8:
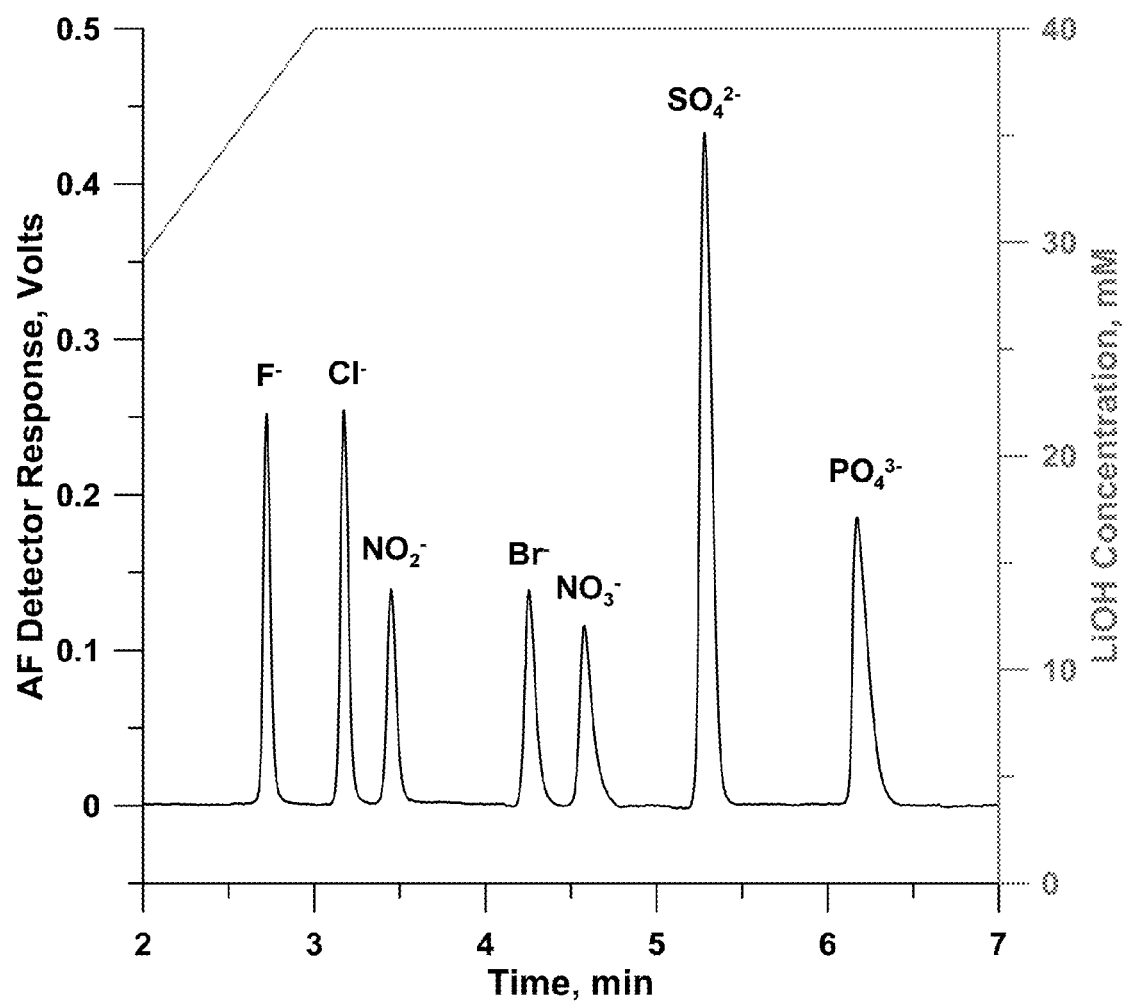
FIG. 8 is gradient chromatogram obtained with suppression (0.65 mm active suppression length) for an analyte mixture containing 100 µM concentrations of each of the labeled anions (except $PO_4^{3-}$, at 200 µM concentration), separated with a linear gradient of electrogenerated LiOH eluent (starting at 8.0 mM at 0 minutes and peaking at 40 mM at 3 minutes) at a flow rate of 168 nL/min. The applied suppression current was 15 µA, and the post-suppression AF detector was operated at 1.2 kHz.

FIG. 7 shows both suppressed ([bottom trace], probed at 9.3 kHz) and unsuppressed ([top trace], probed at 310 kHz) chromatograms, using near-optimal frequencies in terms of peak width as demonstrated in FIG. 6. The additional volume between the detectors results in slightly increased apparent retention times. The first difference is that the massive water dip in the nonsuppressed chromatogram makes it impossible to detect fluoride. The second, unanticipated finding is that the suppressed peaks are actually narrower than the corresponding nonsuppressed peaks as confirmed numerically in Table 3.

TABLE 3

Plate Counts, Suppressed and Nonsuppressed Detector

| | Peak Half-Width, nL | | | Plate Counts | |
|---|---|---|---|---|---|
| | Suppressed | Nonsuppressed | | Suppressed | Nonsuppressed |
| Fluoride | 4.86 ± 0.03 | (ND) | Fluoride | 52,300 ± 500 | (ND) |
| Chloride | 7.11 ± 0.03 | (9.25 ± 0.17) | Chloride | 33,650 ± 90 | 15,800 ± 950 |
| Nitrite | 9.73 ± 0.10 | (11.61 ± 0.24) | Nitrite | 21,300 ± 320 | 12,000 ± 700 |
| Bromide | 15.53 ± 0.54 | (19.35 ± 2.09) | Bromide | 13,100 ± 900 | 7,100 ± 1700 |
| Nitrate | 21.93 ± 0.29 | (24.25 ± 1.32) | Nitrate | 8,000 ± 250 | 5,400 ± 540 |

As the retention times are longer for the suppressed detector, the plate counts (defined simply as $5.54(t_R/W_{1/2})^2$) are relatively even greater. The reason for this "negative" dispersion is not yet understood. In part, this may be due to the nonlinear nature of the response in the conductance domain for unsuppressed detection; if the nonsuppressed signal is related to (concentration)$^n$ where n<1, the peak half-widths will be greater than they actually are [24]. The poor peaks and drifting baselines also make it difficult to accurately measure the half widths. In addition, the Trace-Dec detector uses proprietary signal filtering (which accounts for the strange lack of noise in the unsuppressed chromatograms) that may also in part be responsible for peaks that may be broader than they really are. For both detectors the applicants have observed a dependence of the peak half widths on the probe frequency, decreasing with increasing frequency. However, that cannot explain the apparent negative dispersion, as the unsuppressed detector is actually operated at a much higher frequency.

Eluent Generator Device

Figure 9A:
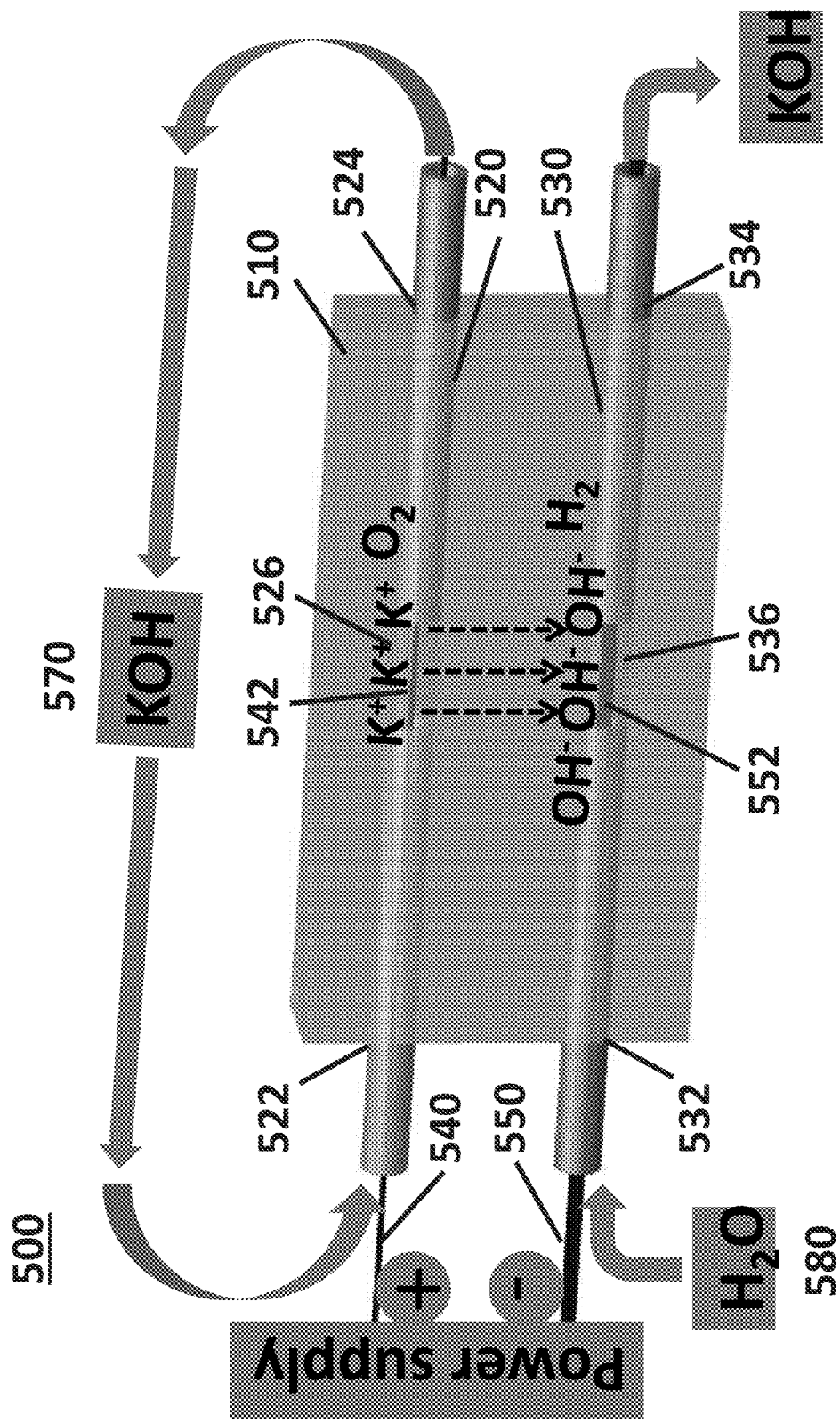
FIG. 9A is a schematic view of an exemplary eluent generator device.

Similar ion exchange polymer block devices may be configured as eluent generator devices. In an exemplary design 500, shown in FIG. 9A, a block of polymer material 510 includes a feed channel 520 and an eluent channel 530. The feed channel 520 is preferably a sub-millimeter diameter channel having an inlet port 522 and an outlet port 524, as well as an active length 526 of exposed polymer material. The eluent channel 530 may similarly be a sub-millimeter channel, including an inlet port 532, an outlet port 534, and an active length 536 of exposed polymer material. The channels 520 and 530, as well as the respective inlet and outlet ports 522-24 and 532-34, may be manufactured using the processes discussed for the regenerant channel(s) of the exemplary suppressor device designs discussed earlier above. Ports 522-24 and 532-34, for example, may be tubes inserted into the block 510 at the respective ends of the channels, e.g., lengths of PTFE tubing for connection to a reservoir 570 of a feed, such as potassium hydroxide, for the feed channel 520 and to a source of deionized water 580 and, optionally a carbonate removal device (Continuously Regenerated Anion Trap Column or CR-ATC, as shown in FIG. 3, serving to remove any adventitious non-hydroxide impurities) for the eluent channel 530, respectively. Methods for insertion similar to those discussed in under the first exemplary design of a suppressor device may be used for insertion of the ports 522-24 and 532-34, with solvent swelling being particularly well suited for use with small scale polymer tubing.

In the illustrated design, a first at-least-partially exposed electrode 540, such as a wire having a non-insulated section or tip 542, extends into the block 510 via the regenerant channel 520, i.e., through at least one of the ports 522-24. A second at-least-partially exposed electrode 550, such as a wire having a non-insulated section or tip 552 extends into the block 510 via the eluent channel 530, likewise through one of the ports 532-34. However, it will be apparent that electrode configurations like those shown in the varying suppressor designs 100-300 may be used. In particular, it will be apparent that an optional third or regenerant channel, like the regenerant channel 270, may be used as an electrode cooling channel, with the second electrode 550 extending into the block 510 via that regenerant channel instead.

Figure 10:
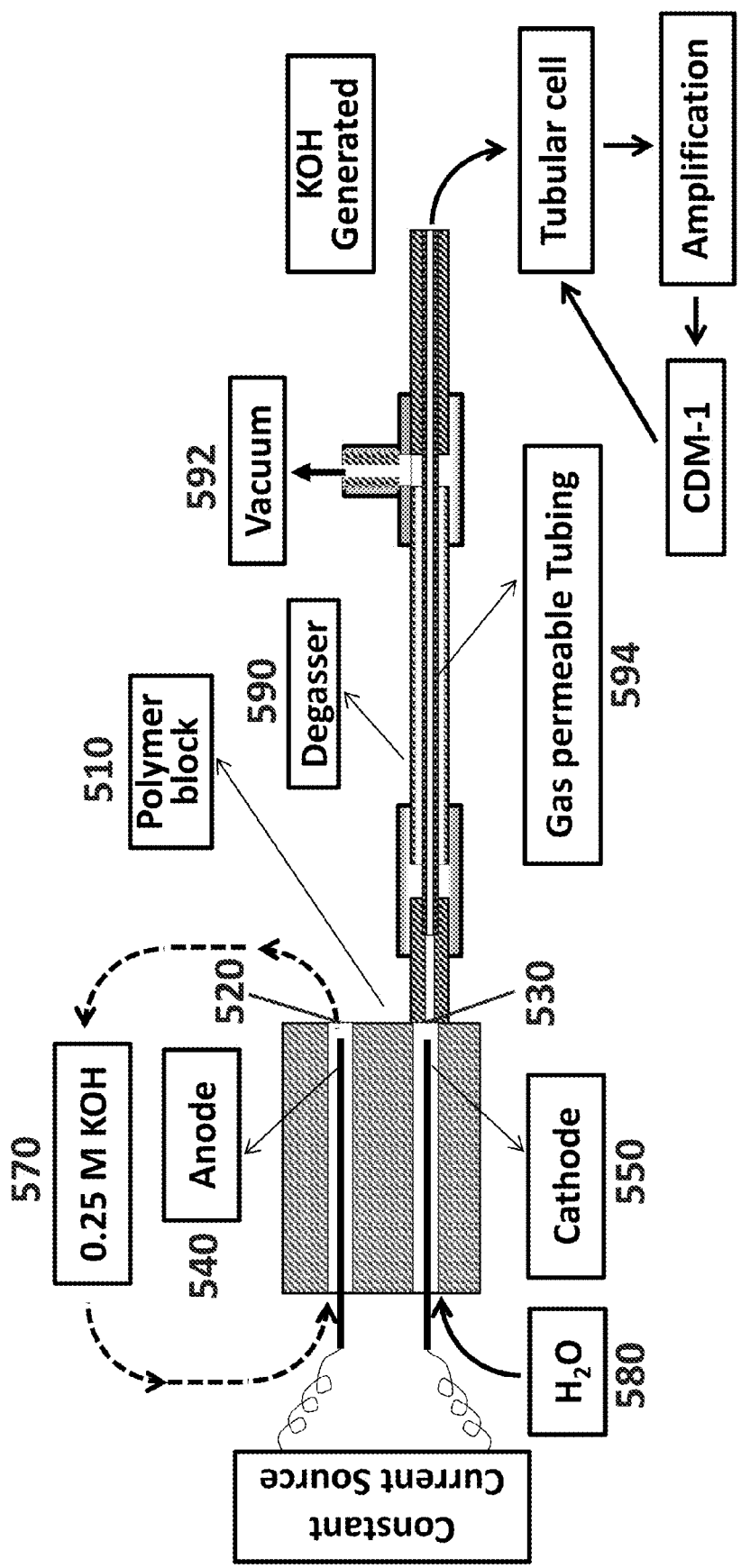
FIG. 10 is a schematic view of an exemplary eluent generation system including a degasser.
Figure 11A:
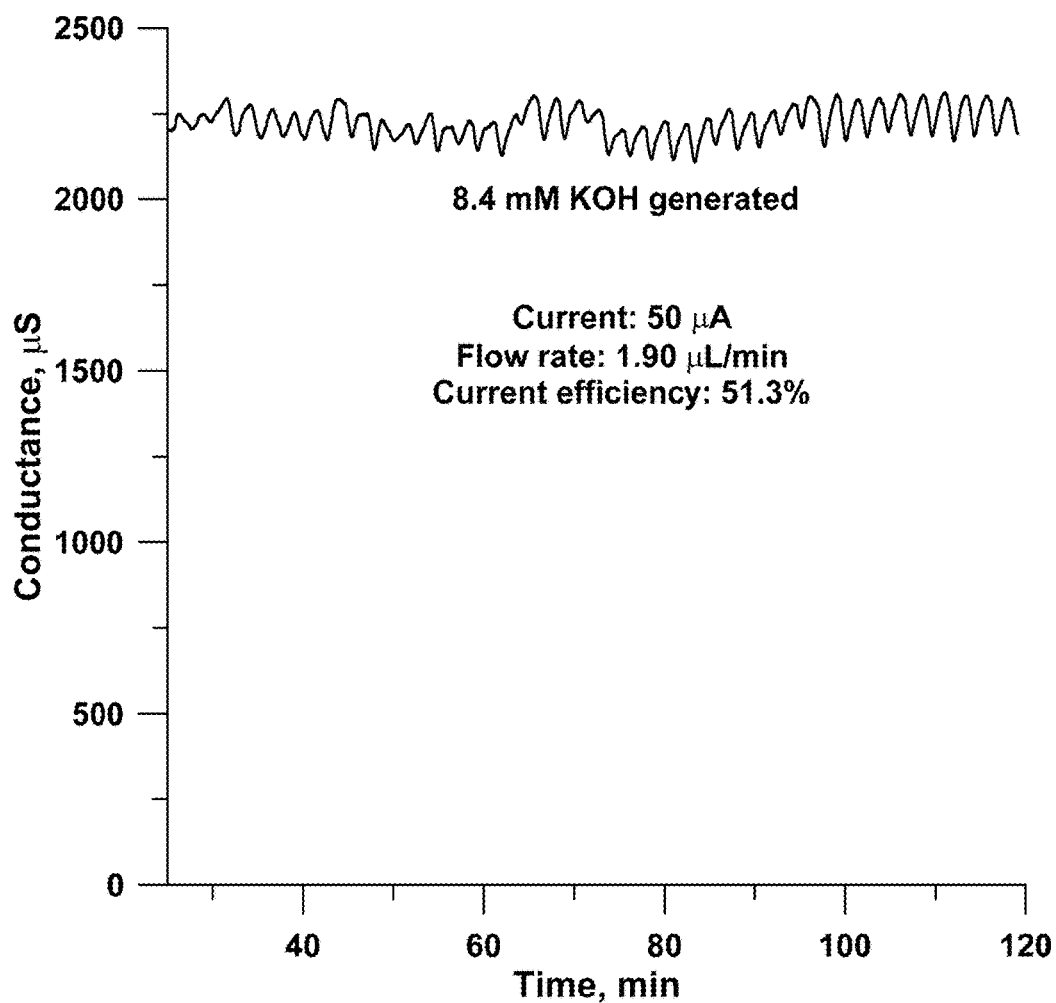
FIGS. 11A-D plot eluent generation capacity versus time under varying exemplary conditions, including.
Figure 11B:
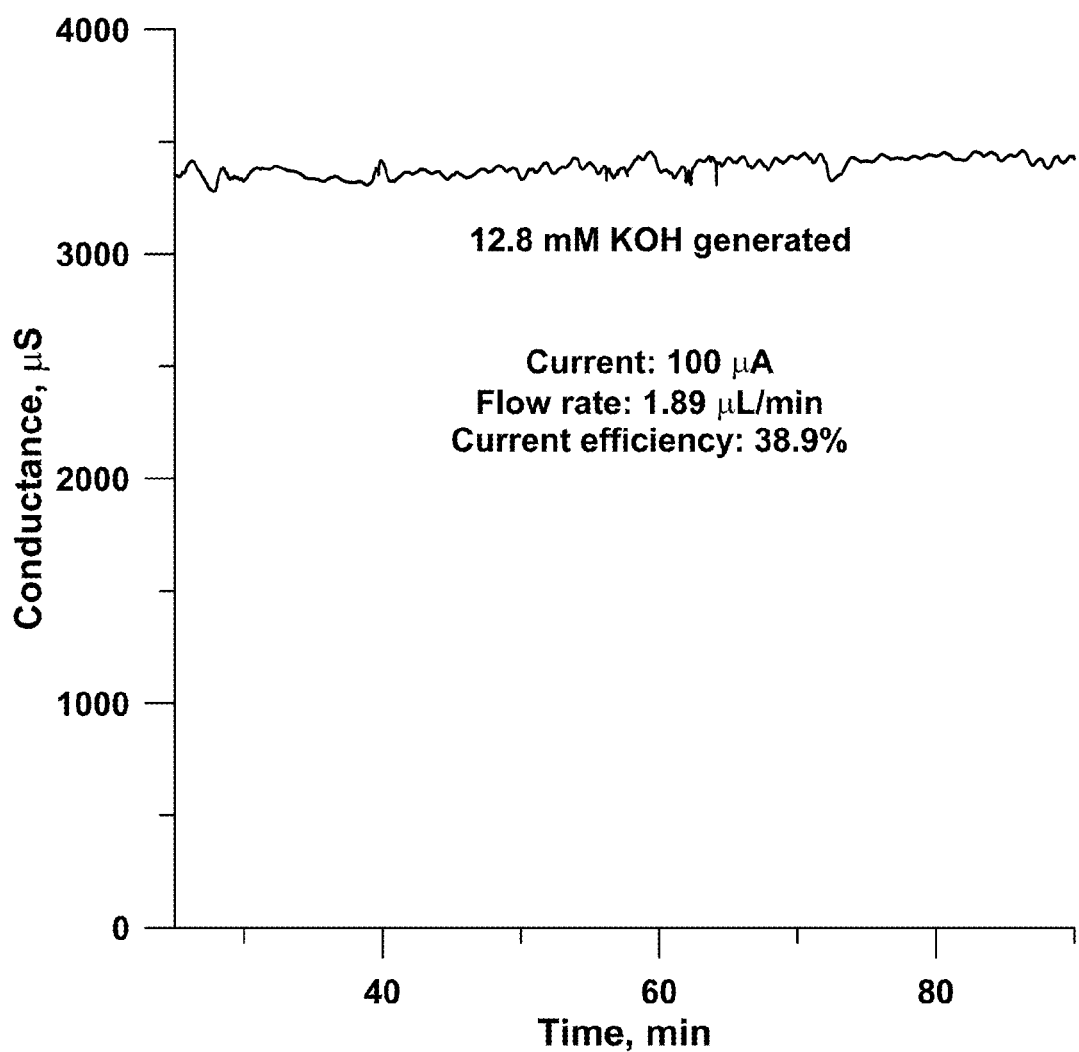
Figure 11C:
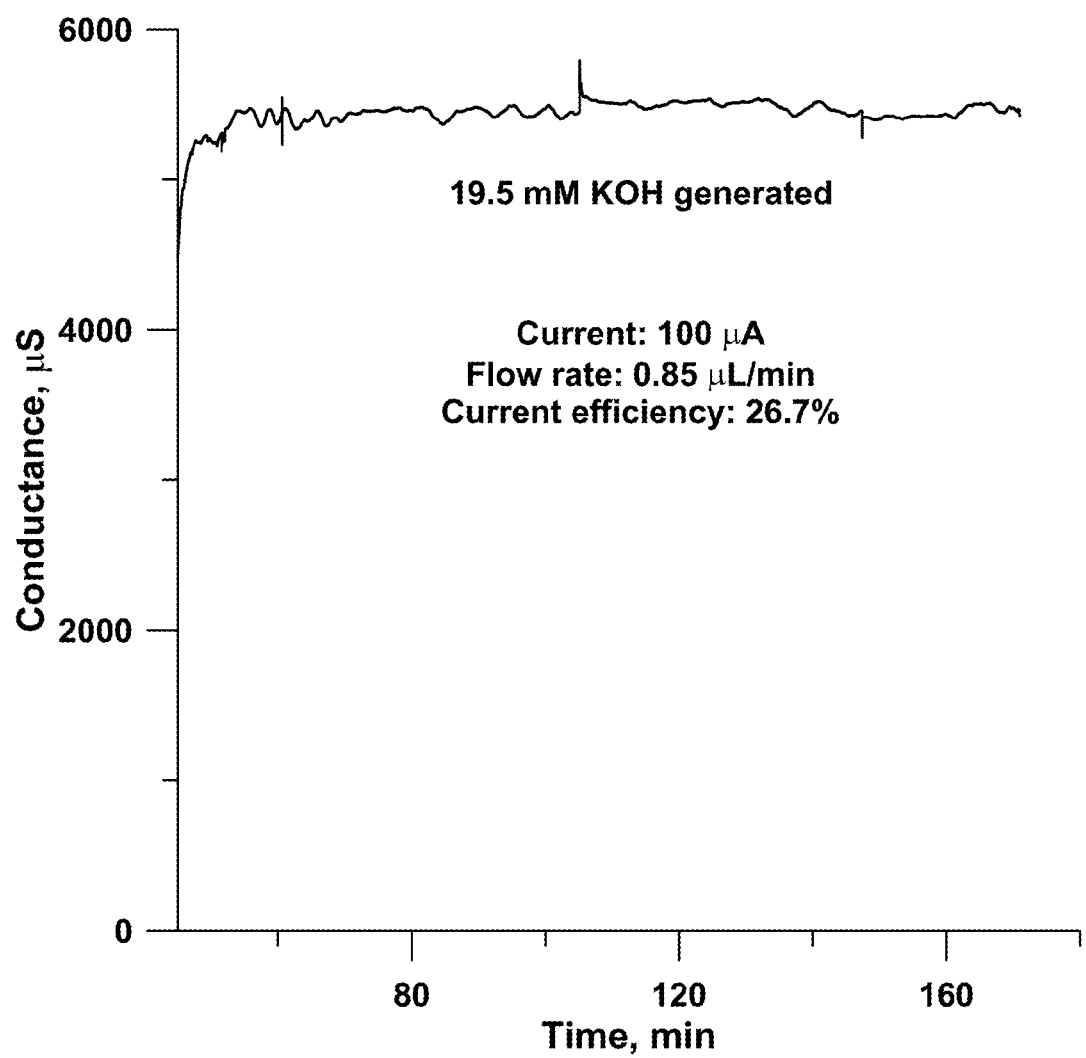
Figure 11D:
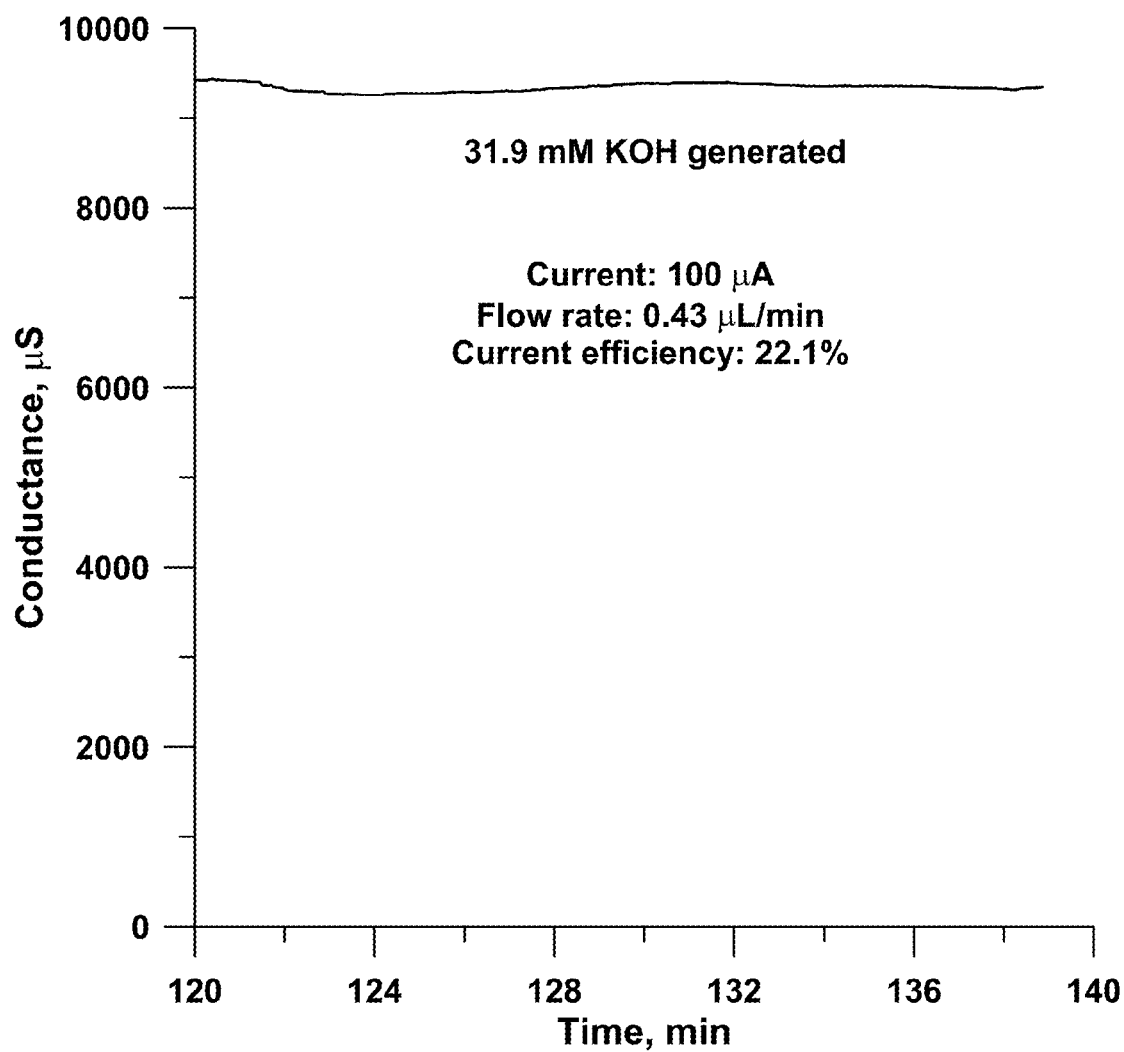

In operation, a feed from reservoir 570 flows through the feed channel 520, while a pure eluent is generated within the eluent channel 530 through the electrodialytic migration of feed ions into the eluent channel and the generation of hydronium or hydroxide counterions within the deionized water provided to the eluent channel. When generating eluents for anion chromatography, cathodically generated hydrogen gas should be removed from the eluent stream before use, which may be accomplished via a degasser 590 such as those used with macroscale eluent generators. An exemplary generator system including degasser that applies a vacuum 592 to draw hydrogen gas across a gas permeable membrane 594 is shown in FIG. 10.

Figure 9B:
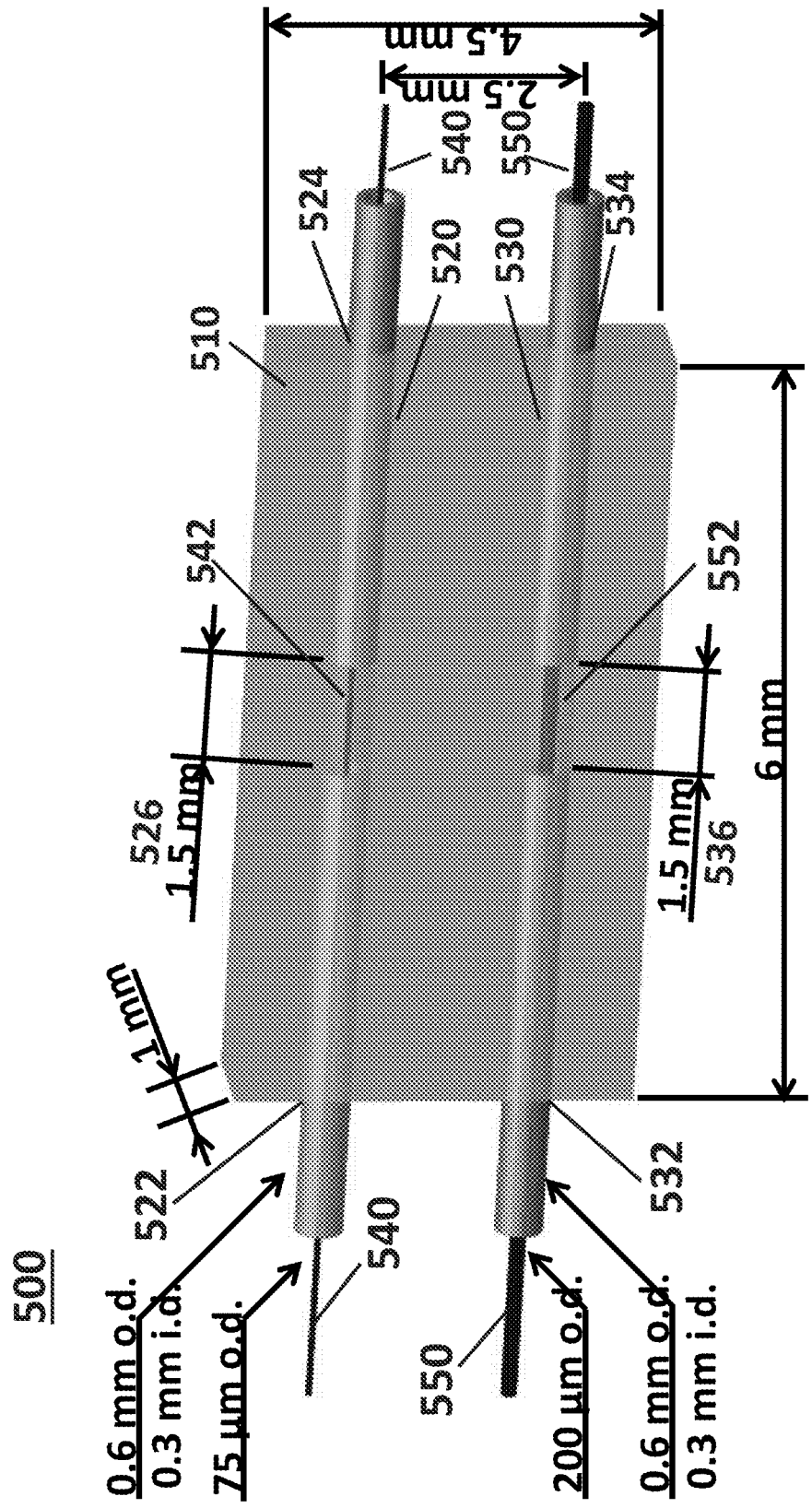
FIG. 9B is a dimensional schematic illustrating exemplary sizing and spacing for elements of the device of FIG. 9A.

FIGS. 11A-D plot the output of a device created with the exemplary dimensional specifications provided in FIG. 9B. Depending upon operating conditions, the device is capable of generating, for example, an eluent stream of 10-40 mM KOH at flow rates well exceeding those required for SCCIC systems:

TABLE 4

Measured KOH eluent strength generated by exemplary device at selected level of constant current across electrodes and water flow rate

| Flow Rate μL/min | KOH generated mM | Current μA | Faradaic Efficiency |
|---|---|---|---|
| 1.9 | 8.4 | 50 | 0.51 |
| 1.9 | 12.8 | 100 | 0.39 |
| 0.85 | 19.5 | 100 | 0.27 |
| 0.43 | 31.9 | 100 | 0.22 |

Figure 12:
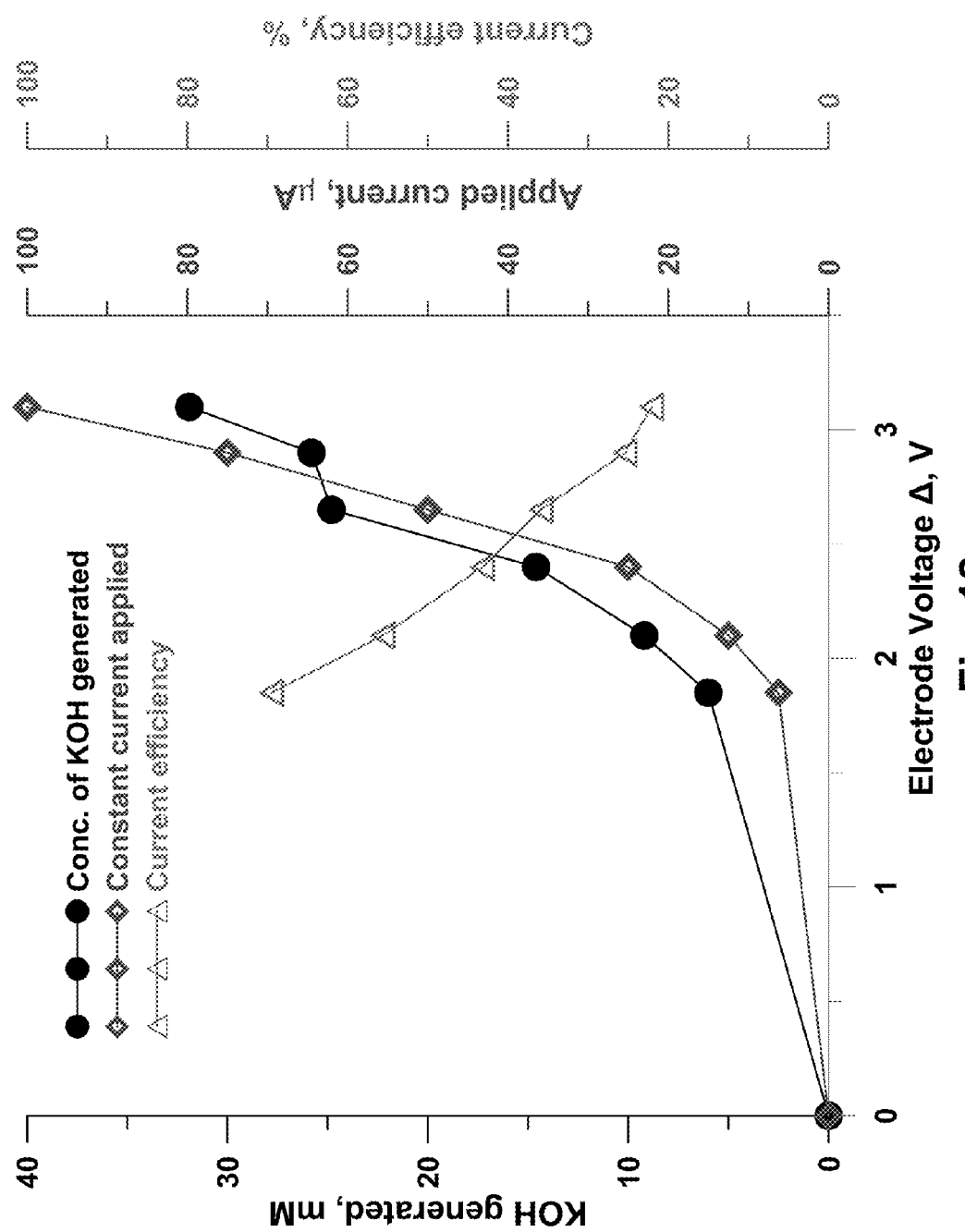
FIG. 12 plots eluent generation capacity and other attributes versus voltage difference across device electrodes for the exemplary device shown in FIGS. 9A and 9B.

In general, as seen in the progression from FIG. 11A to 11D, eluent strength can be altered by changing the applied constant current (within a practical range of 10 to 250 μA due to heat generated at the electrode) and changing the flow rate through the eluent channel 530 (where lowering the flow rate results in a greater concentration within the eluent channel). One disadvantage of the present eluent generator is sub-Faradaic efficiency because current can pass from one electrode to the other directly through the block without going through the fluid channels. FIG. 12 shows how efficiency becomes worse as the applied constant current is increased to generate higher eluent concentrations. However, the device can advantageously enable virtually continuous operation of a SCCIC system, generating eluent from a small stock of recirculated feed eluent, in comparison to the mechanical energy usage and reagent consumption of a system fractionating and recirculating (or, potentially, discarding) a higher flow rate eluent stream in an effort to obtain reliable, sub-μL/min flow rates.

Conclusion

In summary, the applicants have demonstrated a capillary scale electrodialytic suppressor capable of operation with ~25 μm bore open tubular columns with a dispersion small enough to provide attractive performance, comparable to current macroscale systems. Applicants have further demonstrated a capillary scale eluent generator that may be paired with such an electrodialytic suppressor to produce a continuously operable SCCIC system with low eluent consumption and high total energy efficiency. The devices enable the use of open tube capillaries that are extremely small and light and consume very little eluent. Accordingly, systems incorporating the devices are well suited for remote analytical systems, including robotic analytical systems used for terrestrial monitoring and extraterrestrial exploration.

REFERENCES

[1] Small, H.; Stevens, T. S.; Bauman, W. C. Anal. Chem. 1975, 47, 1801-1809.
[2] Haddad, P. R.; Jackson, P. E.; Shaw, M. J. J. Chromatogr. A 2003, 1000, 725-742.
[3] Stevens, T. S.; Davis, J. C.; Small, H. Anal. Chem. 1981, 53, 1488-1492.
[4] Dasgupta, P. K. Anal. Chem. 1984, 56, 103-105.
[5] Stillian, J. LC (Mag.) 1985, 3, 802
[6] Tian, Z. W.; Hu, R. Z.; Lin, H. S.; Hu, W. L. J. Chromatogr. 1988, 439, 151-157.
[7] Rabin, S.; Stillian, J.; Barreto, V.; Friedman, K.; Toofan, M. J. Chromatogr. 1993, 640, 97-109.
[8] Small, H.; Riviello, J. Anal. Chem. 1998, 70, 2205-2212.
[9] Gjerde, D. T.; Benson, J. V. Anal. Chem. 1990, 62, 612-615.
[10] Kuban, P.; Berg, J.; Dasgupta, P. K. Anal. Chem. 2003, 75, 3549-3556. doi:10.1021/ac0340713
[11] Continuous Ion Species Removal Device and Method. Dasgupta, P. K.; Kuban, P.; Berg, J. M. U.S. Pat. No. 7,582,482. 1 Sep. 2009.
[12] Wouters, S.; Wouters, B.; Jespers, S.; Desmet, G.; Eghbali, H.; Bruggink, C.; Eeltink, S. J. Chromatogr. A 2014, 1355, 253-260.
[13] Rokushika, S.; Qiu, Z. Y.; Hatano, H. J. Chromatogr. 1983, 260, 81-87.
[14] Kuban, P.; Dasgupta, P. K. J. Sep. Sci. 2004, 27, 1441-1457.
[15] Huang, W. X.; Hu, R. Z.; Chen, H. B.; Su, Y. H. Analyst 2011, 136, 901-903.
[16] Stevens, T. S.; Jewett, G. L.; Bredeweg, R. A. Anal. Chem. 1982, 54, 1206-1208.
[17] Christian, G. D.; Dasgupta, P. K.; Schug, K. Analytical Chemistry, 7th ed. Wiley, New York, 2014. pp 676.
[18] Yang, B. C.; Zhang, M.; Kanyanee, T.; Stamos, B. N.; Dasgupta, P. K. Anal. Chemistry 2014, 86, 11554-11561.
[19] Dasgupta, P. K.; Bao, L. Anal. Chem. 1993, 65, 1003-1011.
[20] Dasgupta, P. K. ACS Adv. Chem. Ser. 1993, 232, 41-90.
[21] Dasgupta, P. K. Anal. Chem. 1984, 56, 103-105.
[22] Castellan, G. W. Physical Chemistry. Addison-Wesley, London, 1964. pp 588.
[23] Zhang, M.; Stamos, B. N.; Amornthammarong, N.; Dasgupta, P. K. Anal. Chem. 2014, 86, 11,538-11,546
[24] Dasgupta, P. K.; Chen, Y.; Serrano, C. A.; Guiochon, G.; Liu, H.; Fairchild, J. N.; Shalliker, R. A. Anal. Chem. 2010, 82, 10,143-10,150.

What is claimed is:

1. An electrodialytic device for ion chromatography comprising a monolithic block of ionomeric polymer material, the block including:
   a first channel formed within the block, the first channel having an inlet port, an outlet port, and an active length of exposed polymer material disposed therebetween;
   a second channel formed within the block, the second channel having an inlet port, an outlet port, and an active length of exposed polymer material disposed therebetween;
   a first at-least-partially exposed electrode positioned in electrical communication with the second channel; and
   a second at-least-partially exposed electrode positioned in electrical communication with the second channel across from the first at-least-partially exposed electrode.

2. The electodialytic device of claim 1, wherein the active length of the first channel and the active length of the second channel are disposed so that at least 10 percent of a current applied across the first and second electrodes flows across the second channel.

3. The electrodialytic device of claim 1, wherein the ionomeric polymer material principally consists of an ionomer, but includes other polymeric or non-polymeric additives.

4. The electrodialytic device of claim 1, wherein the ionomeric polymer material comprises a perfluorosulfonate cation exchange resin.

5. The electrodialytic device of claim 1, wherein the first channel is a sub-millimeter diameter channel.

6. The electrodialytic device of claim 1, wherein the second channel is a sub-millimeter diameter channel.

7. The electrodialytic device of claim 6, wherein the second channel has been manufactured by cracking the polymer material so as to have a rough-walled average diameter of less than 100 μm.

8. The electrodialytic device of claim 1, wherein the first at-least-partially exposed electrode enters the monolithic block through at least one of the inlet port and outlet port of the first channel.

9. The electrodialytic device of claim 8, wherein the second at-least-partially exposed electrode enters the monolithic block through at least one of the inlet port and outlet port of the second channel.

10. The electrodialytic device of claim 1, wherein the device includes a third channel, the third channel further including an inlet port, an outlet port, and an active length of exposed polymer material disposed therebetween, and wherein the active length of the third channel and the active lengths of the first and second channels overlap so as to permit the electrodialytic migration of ions between the active lengths.

11. The electrodialytic device of claim 10, wherein the second at-least-partially exposed electrode enters the monolithic block through at least one of the inlet port and outlet port of the third channel.

12. The electrodialytic device of claim 1, wherein the active length of the second channel is from 0.4 mm to 1.5 mm long.

13. The electrodialytic device of claim 12, wherein the inlet port of the second channel is a terminal end of a capillary separation column.

14. The electrodialytic device of claim 13, wherein the outlet port of the second channel is an end of a detection capillary associated with a conductometric detector.

15. The electrodialytic device of claim 8, wherein the first at-least-partially exposed electrode has a non-insulated section or tip positioned within the active length of the first channel.

16. The electrodialytic device of claim 15, wherein the first at-least-partially exposed electrode comprises a platinum wire inserted to a depth extending to at least the active length of the first channel.

17. The electrodialytic device of claim 16, wherein the first at-least-partially exposed electrode enters the monolithic block through a first T-arm tubing union serving as the at least one of the inlet port and outlet port of the first channel.

18. The electrodialytic device of claim 11, wherein the second at-least-partially exposed electrode has a non-insulated section or tip positioned within the active length of the third channel.

19. The electrodialytic device of claim 18, wherein the second at-least-partially exposed electrode comprises a platinum wire inserted to a depth extending to at least the active length of the third channel.

20. The electrodialytic device of claim 19, wherein the second at-least-partially exposed electrode enters the monolithic block through a second T-arm tubing union serving as the at least one of the inlet port and outlet port of the third channel.

* * * * *